United States Patent
Gross et al.

(10) Patent No.: US 6,326,354 B1
(45) Date of Patent: *Dec. 4, 2001

(54) MODULATION OF APOPTOSIS WITH BID

(75) Inventors: Atan Gross, St. Louis, MO (US); Stanley J. Korsmeyer, Weston, MA (US)

(73) Assignee: Washington University, St. Louis, MO (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/136,879

(22) Filed: Aug. 19, 1998

(51) Int. Cl.[7] .............................. A61K 38/00; C12N 5/00; C07K 14/435
(52) U.S. Cl. .............................. 514/12; 514/21; 435/375; 530/350
(58) Field of Search .............................. 435/375; 514/12, 514/21; 530/350

(56) References Cited

FOREIGN PATENT DOCUMENTS

WO98/09980    3/1998   (WO).

OTHER PUBLICATIONS

Cosulich et al., Regulation of apoptosis by BH3 domains in a cell–free system, Current Biology, vol. 7 No. 12, pp. 913–920 (Oct. 31, 1997).

Bossy–Wetzel et al., Mitochondrial cytochrome c release in apoptosis occurs upstream of DEVD–specific caspase activation and independently of mitochondrial transmembrane depolarization, EMBO J. 17:37–49 (1998).

Boyd et al., Bik, a novel death–inducing protein shares a distinct sequence motif with Bcl–2 family proteins and interacts with viral and cellular survival–promoting proteins, Oncogene 11:1921–1928 (1995).

Conradt and Horvitz, The C. elegans Protein EGL–1 Is Required for Programmed Cell Death and Interacts with the Bcl–2–like Protein CED–9, Cell 93:519–529 (1998).

Gross et al., Enforced dimerization of BAX results in its translocation, mitochondrial dysfunction and apoptosis, EMBO J. 17:3878–3885 (1998).

Hegde et al., Blk, a BH3–containing Mouse Protein That Interacts with Bcl–2 and Bcl–xL, Is a Potent Death Agonist, J. Biol. Chem. 273:7783–7786 (1998).

Inohara et al., harakiri, a novel regulator of cell death, encodes a protein that activates apoptosis and interacts selectively with survival–promoting proteins Bcl–2 and Bcl–$X_L$,EMBO J. 16:1686–1694 (1997).

Kluck et al., Cytochrome c activation of CPP32–like proteolysis plays a critical role in a Xenopus cell–free apoptosis system, EMBO J. 16:4639–4649 (1997).

O'Connor et al., Bim: a novel member of the Bcl–2 family that promotes apoptosis, EMBO J. 17:384–395 (1998).

Wang et al., BID: a novel BH3 domain–only death agonist, Genes & Dev. 10:2859–2869 (1996).

Wolter et al., Movement of Bax from the Cytosol to Mitochondria during Apoptosis, J. Cell Biol. 139:1281–1292 (1997).

Yang et al., Bad, a Heterodimeric Partner for Bcl–$X_L$ and Bcl–2 Displaces Bax and Promotes Cell Death, Cell 80:285–291 (1995).

Zha et al., Serine Phosphorylation of Death Agonist BAD in Response to Survival Factor Results in Binding to 14–3–3 Not BCL–$X_L$, Cell 87:619–628 (1996).

Zha et al., BH3 Domain of BAD is Required for Heterodimerization with BCL–$X_L$ and Pro–apoptotic Activity, J. Biol. Chem. 272:24101–24104 (1997).

Patent Cooperation Treaty International Search Report for PCT/US99/16966, Feb. 17, 2000.

Gross et al., Journal of Biological Chemicstry, vol. 274, No. 2, pp. 1156–1163, XP–002127459, Caspase Cleaved BID Targets Mitochondria and Is Required for Cytochrome c Release, while BCL–$X_L$ Prevents This Release but Not Tumor Necrosis Factor–R1/Fas Death, Jan. 8, 1999.

Li et al., Cell, vol. 94, p. 491–501, XP–002127460, Cleavage of BID by Caspage 8 Mediates the Mitochondrial Damage in the Fas Pathway of Apoptosis, Aug. 21, 1998.

Kuwana et al., Journal of Biological Chemistry, vol. 273, No. 20, pp. 16589–16594, Apoptosis Induction by Caspage–8 Is Amplified through the Mitochondrial Release of Cytochrome c, Jun. 26, 1998.

Thornberry et al., Journal of Biological Chemistry, vol. 272, No. 29, pp. 17907–17911, XP–002127462, A Combinatorial Approach Defines Specificities of Members of the Caspase Family and Granzyme B, Jul. 19, 1997.

Primary Examiner—David Saunders
Assistant Examiner—Mary Beth Tung
(74) Attorney, Agent, or Firm—Howell & Haferkamp LC

(57) ABSTRACT

A novel p15 BID polypeptide having cell death agonist activity is disclosed. The p15 BID polypeptide is produced by caspase-cleavage of BID in cells undergoing cell death mediated by TNF or FAS receptors. The p15 BID is useful in methods for modulating death of a target cell which comprise treating the cell with p15 BID. Methods for inhibiting cell death are also described which involve treating a target cell with a mutant p15 BID lacking cell death agonist activity.

6 Claims, 18 Drawing Sheets

```
huBid  - MDCEVNNGSSLRDECITNLLVFGFLQSCSDNSFRRELDALGHELPVLAPQ     - 50
         || ||| |||  || ||||||||||||| ||  || ||  |||| ||||
muBid  - MDSEVSNGSGLGAKHITDLLVFGFLQSSG--CTRQELEVLGRELPV-QAY      - 47

BH3
huBid  - WEGY--DELQTDGNRSSHS-RLGRIEADSESQEDIIRNIARHLAQVGDSM      - 97
         ||    |||||||| || | ||||| | |||||| ||||||||||| ||| ·|·
muBid  - WEADLEDELQTDGSQASRSFNQGRIEPDSESQEEIIHNIARHLAQIGDEM      - 97

┌─────────
huBid  - │DRSIPPGLVNGLALQLRNTSRSEEDRNRDLATALEQLLQAYPRDMEKEKT     - 147
         │|  ||· |· ||   ||  || · |·||·||| ·||·||||||||| ·|·
muBid  - │DHNIQPTLVRQLAAQFMNGSLSEEDKRNCLAKALDEVKTAFPRDMENDKA     - 147
         └───────── huBid  - MLVLALLLAKKVASHTPSLLRDVFHTTVNFINQNLRTYVRSLARNGMD        - 195
         || · · ||||||||||·· |||||||||||||||| ||| |||· |||
muBid  - MLIMTMLLAKKVASHAPSLLRDVFHTTVNFINQNLFSYVRNLVRNEMD        - 195
```

FIGURE 1

HUMAN p15 BID

| | | | | | | | | | | | | | |
|---|---|---|---|---|---|---|---|---|---|---|---|---|---|
| Gly 1 | Asn | Arg | Ser | Ser 5 | His | Ser | Arg | Leu | Gly 10 | Arg | Ile | Glu | Ala | Asp 15 | Ser |

Gly Asn Arg Ser Ser His Ser Arg Leu Gly Arg Ile Glu Ala Asp Ser
1               5                       10                  15

Glu Ser Gln Glu Asp Ile Ile Arg Asn Ile Ala Arg His Leu Ala Gln
                20              25                  30

Val Gly Asp Ser Met Asp Arg Ser Ile Pro Pro Gly Leu Val Asn Gly
        35                  40                  45

Leu Ala Leu Gln Leu Arg Asn Thr Ser Arg Ser Glu Glu Asp Arg Asn
    50                  55                  60

Arg Asp Leu Ala Thr Ala Leu Glu Gln Leu Leu Gln Ala Tyr Pro Arg
65                  70                  75                  80

Asp Met Glu Lys Glu Lys Thr Met Leu Val Leu Ala Leu Leu Leu Ala
                85                  90                  95

Lys Lys Val Ala Ser His Thr Pro Ser Leu Leu Arg Asp Val Phe His
            100                 105                 110

Thr Thr Val Asn Phe Ile Asn Gln Asn Leu Arg Thr Tyr Val Arg Ser
        115                 120                 125

Leu Ala Arg Asn Gly Met Asp
    130             135

FIGURE 2A

HUMAN VARIANT p15 BID

```
Gly Asn Arg Ser Ser His Ser Arg Leu Gly Arg Ile Glu Ala Asp Ser
1               5                   10                  15

Glu Ser Gln Glu Asp Ile Ile Arg Asn Ile Ala Arg His Leu Ala Gln
                20                  25                  30

Val Gly Asp Ser Met Asp Arg Ser Ile Pro Pro Gly Leu Val Asn Gly
            35                  40                  45

Leu Ala Leu Gln Leu Arg Asn Thr Ser Arg Ser Glu Glu Asp Arg Asn
    50                  55                  60

Arg Asp Leu Ala Thr Ala Leu Glu Gln Leu Leu Gln Ala Tyr Pro Arg
65                  70                  75                  80

Asp Met Glu Lys Glu Lys Thr Met Leu Val Leu Ala Leu Leu Leu Ala
                85                  90                  95

Lys Lys Val Ala Ser His Thr Pro Ser Leu Leu Arg Asp Val Phe His
            100                 105                 110

Thr Thr Val Asn Phe Ile Asn Gln Asn Leu Arg Thr Tyr Val Arg Ser
            115                 120                 125

Leu Ala Arg Asn Val Arg Thr Leu Glu Gly Met Asp
    130                 135                 140
```

FIGURE 2B

MURINE p15 BID

| | | | | | | | | | | | | | | |
|---|---|---|---|---|---|---|---|---|---|---|---|---|---|---|
|Gly|Ser|Gln|Ala|Ser|Arg|Ser|Phe|Asn|Gln|Gly|Arg|Ile|Glu|Pro|Asp|
|1| | | |5| | | |10| | | | |15| |
|Ser|Glu|Ser|Gln|Glu|Glu|Ile|Ile|His|Asn|Ile|Ala|Arg|His|Leu|Ala|
| | | |20| | | |25| | | | |30| | | |
|Gln|Ile|Gly|Asp|Glu|Met|Asp|His|Asn|Ile|Gln|Pro|Thr|Leu|Val|Arg|
| | |35| | | |40| | | | |45| | | | |
|Gln|Leu|Ala|Ala|Gln|Phe|Met|Asn|Gly|Ser|Leu|Ser|Glu|Glu|Asp|Lys|
| |50| | | |55| | | | |60| | | | | |
|Arg|Asn|Cys|Leu|Ala|Lys|Ala|Leu|Asp|Glu|Val|Lys|Thr|Ala|Phe|Pro|
|65| | | |70| | | | |75| | | | | |80|
|Arg|Asp|Met|Glu|Asn|Asp|Lys|Ala|Met|Leu|Ile|Met|Thr|Met|Leu|Leu|
| | | | |85| | | |90| | | | |95| | |
|Ala|Lys|Lys|Val|Ala|Ser|His|Ala|Pro|Ser|Leu|Leu|Arg|Asp|Val|Phe|
| | | |100| | | |105| | | | |110| | | |
|His|Thr|Thr|Val|Asn|Phe|Ile|Asn|Gln|Asn|Leu|Phe|Ser|Tyr|Val|Arg|
| | |115| | | |120| | | | |125| | | | |
|Asn|Leu|Val|Arg|Asn|Glu|Met|Asp| | | | | | | | |
| |130| | | |135| | | | | | | | | | |

FIGURE 2C

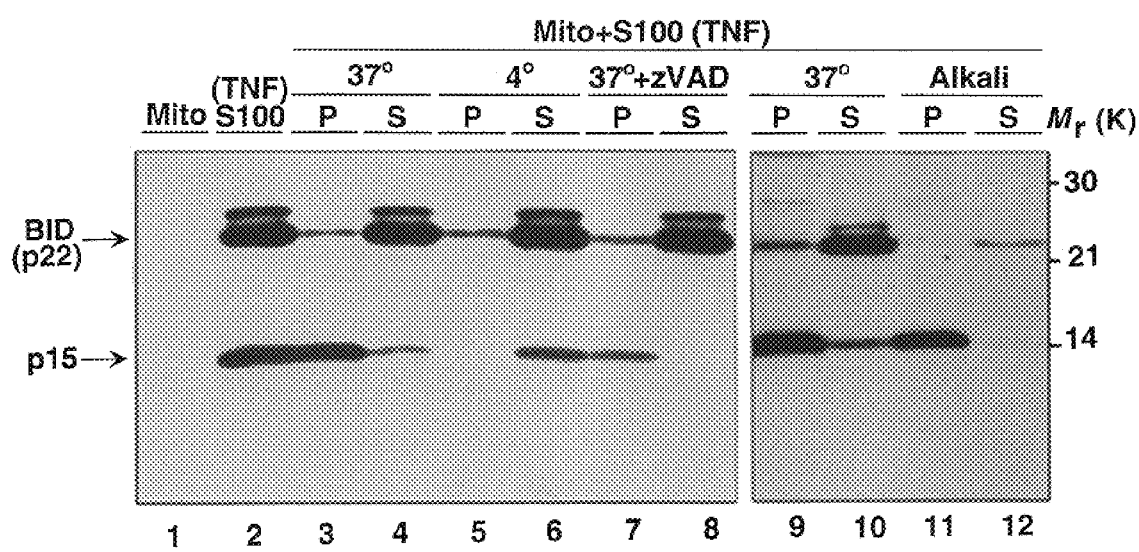

FIGURE 6C
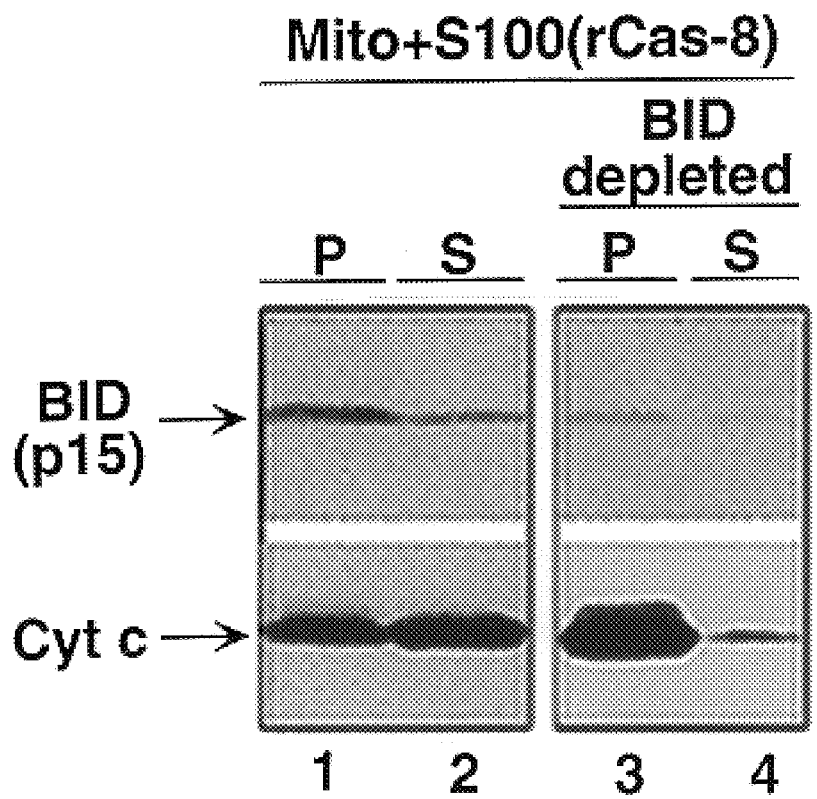
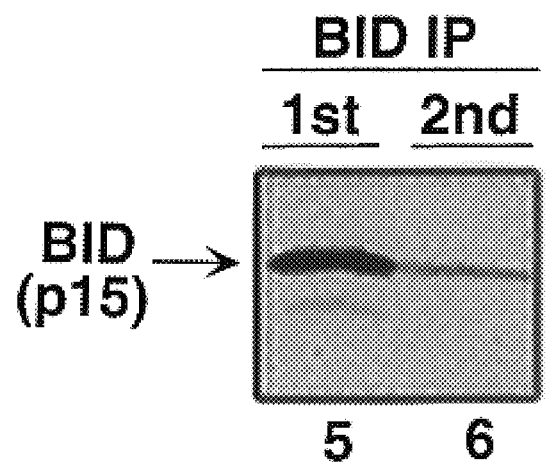

MODULATION OF APOPTOSIS WITH BID

REFERENCE TO GOVERNMENT GRANT

This invention was made with government support under Grant Number CA 50239-10. The government has certain rights in this invention.

BACKGROUND OF THE INVENTION

(1) Field of the Invention

This invention relates generally to the regulation of cell death and to compounds which regulate cell death, and more particularly, to a novel BH3-containing fragment of BID with cell death agonist activity.

(2) Description of the Related Art

Programmed cell death, or apoptosis, is critical for the successful crafting of multiple lineages, the maintenance of normal tissue homeostasis and a non-inflammatory response to toxic stimuli (Thompson, Science 167:1456–1462, 1995). A distinct genetic pathway apparently shared by all multicellular organisms governs apoptosis. The BCL-2 family of proteins constitutes a decisional checkpoint within the common portion of this pathway. Full members of the BCL-2 family share homology in four conserved domains designated BHI, BH2, BH3 and BH4 (Farrow and Brown, Curr. Opin. Genet. Dev. 6:45–49, 1996). The multi-dimensional NMR and X-ray crystallographic structure of a BCL-$X_L$ monomer indicated that BH1, BH2 and BH3 domains represent α helices in close proximity which create a hydrophobic pocket presumably involved in interactions with other BCL-2 family members (Muchmore et al., Nature 381:335–341, 1996).

The BCL-2 family possesses pro-apoptotic (BAX, BAK, BOK) as well as anti-apoptotic (BCL-2, BCL-$X_L$, BCL-W, MCL-1, A1) molecules (Farrow and Brown, supra). The ratio of anti- to pro-apoptotic molecules such as BCL-2/BAX determines the response to a death signal (Oltvai et al., Cell 74:609–619, 1993). A striking characteristic of many BCL-2 family members is their propensity to form homo- and heterodimers (Sedlak et al., Proc. Natl. Acad. Sci. USA 92:7834–7838, 1995; Zha et al., J. Biol. Chem. 271, 7440–7444, 1996). The NMR analysis of a BCL-$X_L$/BAK BH3 peptide complex revealed both hydrophobic and electrostatic interactions between the BCL-$X_L$ pocket and a BH3 amphipathic a-helical peptide from BAK (Sattler et al., Science 275:983–986, 1997). Results of deletion analysis within BAK (Chittenden et al., EMBO J. 14:5589–5596, 1995) as well as an extensive mutational analysis of BAX (Wang et al., Mol. Cell. Biol., 1998, in press) indicate that the BH3 domain serves as a minimal "death domain" critical for both dimerization and killing.

A divergent subset of the BCL-2 family possesses sequence homology only to the BH3 amphipathic α helical domain. These "BH3 only" members include the mammalian proteins BID, BAD, BIK, RIM, BLK and HRK, as well as the EGL-1 protein of C. elegans. Of note, all of these molecules are pro-apoptotic, lending credence to the thesis that BH3 represents a minimal death domain (Wang et al., Genes & Dev. 10:2859–2869, 1996; Yang et al., Cell 80:285–291, 1995; Boyd et al., Oncogene 11 :1921–1928, 1995; O'Connor et al., EMBO J. 17:384–395, 1998; Hegde et al., J. Biol. Chem. 273:7783–7786, 1998; Inohara et al., EMBO J. 16:1686–1694 1997; Conradt and Horvitz, Cell 93:519–529, 1998). Where examined, these "BH3 only" molecules are capable of heterodimerizing with classic BCL-2 family members. Mutagenesis of the BH3 domain of BID (Wang et al., 1996, supra; copending U.S. application Ser. No. 08/706,741) and BAD (Zha et al., J. Biol. Chem. 272:24101–24104, 1997) indicated that BH3 was essential for these interactions as well as the killing activity.

BID and BAD lack the typical hydrophobic C-terminal sequence that is found in most BCL-2 family members, which for BCL-2 has been shown to function as a signal anchor segment required for its targeting mitochondria (Nguyen et al., J. Biol. Chem. 268:25265–25268, 1993). Consistent with their lack of a putative C-terminal anchor segment, BID and BAD have been observed in cytosolic as well as membrane based localizations (Wang et al., 1996, supra; Zha et al., Cell 87:619–628, 1996). It has been suggested that BID and BAD may represent death ligands, sensors that receive death signals in the cytosol and translocate to membranes where they interact with membrane bound, classic BCL-2 members which serve as "receptors" (Wang et al., 1996, supra).

This model was supported by the demonstration that in the presence of the survival factor IL-3, cells inactivate BAD by phosphorylation (Zha et al., 1996, supra). Its phosphorylation status has the dual impact of dictating BAD's location as well as its binding partners. Phosphorylated BAD is sequestered in the cytosol bound to 14-3-3; whereas, only the active non-phosphorylated BAD heterodimerizes with BCL-$X_L$ or BCL-2 at membrane sites to promote cell death (Zha et al., 1996, supra).

Recently, pro-apoptotic BAX, despite possessing a hydrophobic C-terminus, has been observed in the soluble fraction of cells as well as mitochondrial membranes (Wolter et al., J. Cell Biol. 139:1281–1292, 1997; Gross et al., EMBO J. 17:3878–3885, 1998). Induced BAX expression (Xiang et al., 1996) or the enforced dimerization of BAX (Gross et al., supra) results in a downstream program of mitochondrial dysfunction as well as caspase activation. A physiologic death stimulus, the withdrawal of IL-3, results in the translocation of monomeric BAX from the cytosol to the mitochondria where it is present as a homodimerized, integral membrane protein (Gross et al., supra).

The importance of the BH3 domain and caspase activation in apoptosis is also suggested by the recent demonstration that BAX and BID fragments containing the B3 domain, i.e., BAX 53-104 and BID 74-128, had death agonist activity when expressed in cells and that death of these cells was significantly inhibited in the presence of the general caspase inhibitor z-VAD-fmk (copending application, U.S. Ser. No. 08/946,039).

The best characterized signal transduction pathways that mediate apoptosis are the cell surface receptors of the TNF family, including CD95 (Fas/Apo-1) and CD120a (p55 TNF receptor) (Tartaglia et al., Cell 74:845–853, 1993; Nagata, Curr. Biol. 6:1241–1243, 1996; Wallach et al., Curr. Opin. Immunol. 10:279–288, 1998). Engagement of Fas/TNF receptor leads to formation of a protein complex known as the DISC (Death-Inducing Signaling Complex) (Medema et al., EMBO J. 16:2794–2804, 1997; Boldin et al., Cell 85:803–815, 1996; Muzio et al., Cell 85:817–827, 1996). This complex comprises Fas/TNF receptor, FADD (MORTI), and pro-caspase-8 (MACH/FLICE/Mch5). Once caspase-8 is recruited, it is processed and released from the complex in active form to activate downstream "effector" caspases (Medema et al., supra; Srinivasula et al., Proc. Natl. Acad. Sci. USA 93:14486–14491, 1996; Muzio et al., J. Biol. Chem. 272:2952–2956, 1997).

The caspase family has been divided into three groups based upon sequence homology and substrate specificity using a positional scanning substrate combinatorial library (Thornberry et al., *J. Biol. Chem.* 272:17907–17911, 1997). The specificity of caspases 2, 3 and 7 for DEXD (SEQ ID NO:6), where X can be any amino acid, suggests they function at the effector phase of apoptosis. In contrast, the optimal cleavage sequence for caspases 6, 8, and 9 of (I/L/V)EXD resembles activation sites in the effector caspase proenzymes, suggesting that caspases 6, 8, and 9 represent "initiator" caspases.

Wang and colleagues described a cell free system of apoptosis, in which S100 extracts of untreated HeLa cells induced the activation of caspase-3 and DNA fragmentation upon addition of dATP (Liu et al., *Cell* 86:147–157, 1996). Further purification of the cytosol identified cytochrome c, which was released from the mitochondria during hypotonic lysis of the cells. Apaf-1, a mammalian homolog of CED-4, was a second factor isolated and required for caspase activation (Zou et al., *Cell* 90:405–413, 1997). Recently, it has been demonstrated that cytochrome c, Apaf-1 and caspase-9 form a complex that initiates a downstream apoptotic caspase cascade (Li et al., *Cell* 91:479–489, 1997). In addition, it was observed that when Xenopus egg cytosol was incubated with isolated mitochondria, cytochrome c was released, leading to the activation of caspases and nuclear apoptosis (Kluck et al., *EMBO J.* 16:4639–4649, 1997). The phenomena of cytochrome c redistribution from mitochondria to cytosol was also reported to occur in intact cells during apoptosis (Bossy-Wetzel et al., *EMBO J.*: 17:37–49, 1998). However, until the studies reported herein, the molecular mechanism responsible for the release of cytochrome c from mitochondria to the cytosol during apoptosis was not known.

Some disease conditions are believed to be related to the development of a defective down-regulation of apoptosis in the affected cells. For example, neoplasias may result, at least in part, from a apoptosis-resistant state in which cell proliferation signals inappropriately exceed cell death signal. Furthermore, some DNA viruses such as Epstein-Barr virus, African swine fever virus and adenovirus, parasitze the host cellular machinery to drive their own replication and at the same time block apoptosis to repress cell death and allow the target cell to reproduce the virus. Moreover, certain disease conditions such as lymphoproliferative conditions, cancer including drug resistant cancer, arthritis, inflammation, autoimmune diseases and the like may result from a down regulation of cell death regulation. In such disease conditions it would be desirable to promote apoptotic mechanisms and one advantageous approach might involve treatment with a cell death agonist having a BH3 domain which has been identified as being critical for killing.

Conversely, in certain disease conditions it would be desirable to inhibit apoptosis such as in the treatment of immunodeficiency diseases, including AIDS, senescence, neurodegenerative disease, ischemic and reperfusion cell death, infertility, wound-healing, and the like. In the treatment of such diseases it would be desirable to diminish the cell death agonist activity of endogenous proteins containing BH3 domains.

Thus it would be desirable to further elucidate how BCL-2 family members, particularly BH3 only family members, regulate apoptosis and to use this knowledge as a basis for treatment modalities to advantageously modulate the apoptotic process in disease conditions involving either inappropriate repression or inappropriate enhancement of cell death.

SUMMARY OF THE INVENTION

In accordance with the present invention it has been discovered that activation of the TNF and FAS death signal pathways induces a caspase-mediated cleavage of cytosolic BID to produce a BID polypeptide fragment of approximately 15 kDa containing the BH3 domain. This polypeptide fragment, referred to herein as p15 BID, translocates from the cell cytosol to the mitochondria where it resides as an integral membrane protein and is required for the release of cytochrome c. N-terminal sequence analysis of p15 produced by incubation of full-length BID, also referred to herein as p22 BID, with Caspase-8 or Caspase-3 demonstrated that BID is cleaved between Asp and Gly residues corresponding to positions 60 and 61 of human BID (SEQ ID NO:1) and 59 and 60 of murine BID (SEQ ID NO:2) (see FIG. 1). Mutation of Asp59 to Ala in murine BID prevents caspase-mediated cleavage at this site.

Therefore, in one aspect the invention provides an isolated and purified polypeptide comprising a p15 BID polypeptide which has cell death agonist activity. Preferred p15 BID polypeptides identified herein include human and murine p15 BID as shown in FIGS. 2A and 2C (SEQ ID NO:3 and SEQ ID NO:5, respectively).

In another embodiment, the invention provides isolated and purified polynucleotides encoding a p15 BID polypeptide having cell death agonist activity. These polynucleotides may be used to transfect a target cell in which expression of the encoded p15 BID polypeptide promotes death of the target cell.

A recombinant cell stably transformed with a polynucleotide encoding for expression a p15 BID polypeptide is also provided by the invention. The recombinant cell may be used in a method for producing the p15 BID polypeptide.

In another embodiment, the present invention provides a composition comprising a p15 BID polypeptide which has cell death agonist activity and a carrier which facilitates delivery of the p15 polypeptide into a cell.

The invention also provides a method for promoting death of a target cell which comprises treating the cell with an effective amount of a p15 BID polypeptide having cell death agonist activity. The cell can be treated in vitro or in vivo in a patient. In one embodiment, the cell is treated in vivo by administering to the patient a polynucleotide encoding the p15 BID polypeptide, through which the p15 polypeptide is expressed in the target cell. Alternatively, the treating step comprises administering the p15 BID polypeptide to the patient, preferably with a carrier that facilitates delivery of the p15 BID polypeptide into the target cell.

In another aspect, the invention is directed to inhibiting cell death using compositions and methods which inhibit the in vivo generation of p15 BID and/or translocation of p15 BID to the mitochondria.

Accordingly, in yet another embodiment the invention provides a composition comprising an agent that specifically inhibits cleavage of p22 BID at the p15 cleavage site and a pharmaceutically acceptable carrier. One such agent is a peptide comprising LQTD (SEQ ID NO:7) which is believed can act as a competitive inhibitor for the active site of Caspase-8 and would thus inhibit Caspase-8 cleavage of p22 BID. The agent may also be a peptide mimetic of LQTD (SEQ ID NO:7).

The invention also provides a method for inhibiting death of a target cell comprising treating the cell with a polynucleotide encoding a mutant p22 BID polypeptide comprising a mutation in the p15 cleavage site which blocks caspase cleavage at the p15 site. The mutation is designed to not significantly reduce binding of the mutant p22 BID to caspases and therefore can act as a competitive inhibitor for Caspase-8 binding to wild-type p22 BID.

In still another embodiment, the invention provides a method for inhibiting death of a target cell comprising treating the cell with a mutant p15 BID polypeptide having an inactivating mutation in the BH3 domain. The mutant p15 BID lacks cell death agonist activity but is capable of serving as a competitive inhibitor in the cellular mechanism which translocates p15 BID to the mitochondria. In one embodiment, the target cell is treated with a mutant p22 BID polypeptide which is cleaved by Caspase-8 to produce mutant p15 BID. The mutant p15 BID and or mutant p22 BID may be delivered to the target cell with a carrier which facilitates entry of the mutant polypeptide into the cell or alternatively may be expressed in the cell by a recombinant polynucleotide introduced into the cell.

Among the several advantages found to be achieved by the present invention, therefore, may be noted the provision of a new p15 BID polypeptide having cell death agonist activity; the provision of polynucleotides encoding p15 BID; the provision of p15 BID or mutant p15 BID compositions which can be readily delivered intracellularly to produce a death agonist or death antagonist activity, respectively; the provision of methods for modulating cell death using these compositions; and the provision of methods for inhibiting cell death by inhibiting in vivo production of p15 BID.

BRIEF DESCRIPTION OF THE DRAWINGS

FIG. 1 illustrates the aligned human and murine BID polypeptides (SEQ ID NOS:1–2) with the caspase cleavage site indicated by an arrow and the BH3 domain boxed;

FIG. 2 illustrates the amino acid sequences of (FIG. 2A) human p15 BID (SEQ ID NO:3), (FIG. 2B) a human variant p15 BID (SEQ ID NO:4) containing an additional five amino acids indicated by the underline, and (FIG. 2C) murine p15 BID (SEQ ID NO:5);

FIG. 5C is a digitized image of a Western blot showing that cytosolic p15 BID targets mouse liver mitochondria but full-length p22 BID does not;

FIGS. 6A–6C are digitized images of Western blots showing that targeting of cytosolic p15 BID to mouse liver mitochondria is required to release cytochrome c;

DETAILED DESCRIPTION OF THE INVENTION

Figure 3A:
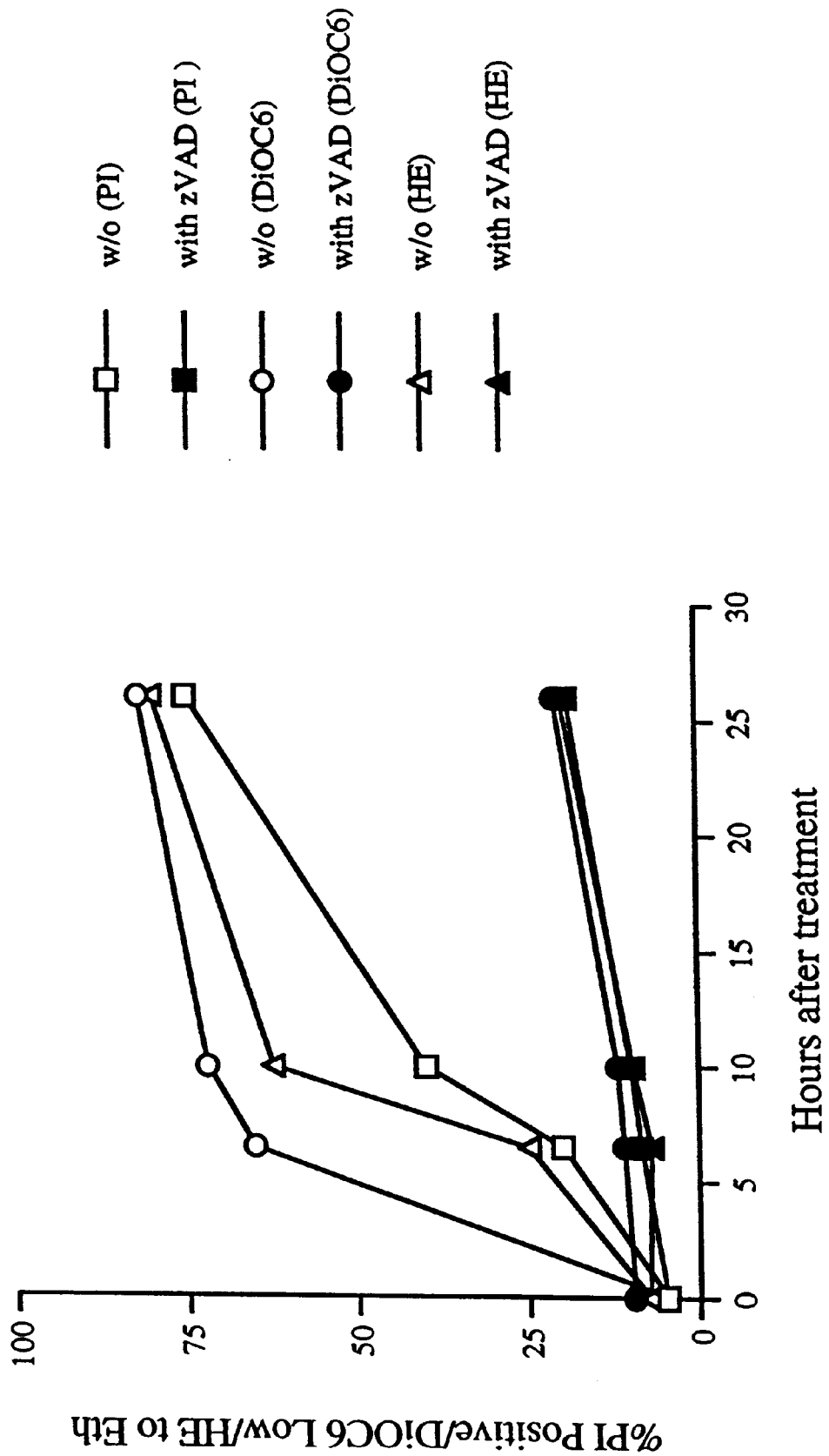
FIG. 3A is a graph showing cell viability, mitochondrial membrane potential and ROS production for cells treated with TNFα/cycloheximide in the presence or absence (w/o) of the general caspase inhibitor zVAD-fmk.

The present invention is based on the surprising discovery that cell death mediated by the TNF and FAS signaling pathways includes the generation of a p15 BID polypeptide which is translocated to the mitochondria where it exerts cell death agonist activity, probably by inducing the release of cytochrome c. The cell death induced by p15 BID is intended to include death by apoptosis and/or death by necrosis. Although the sequence of biochemical and molecular events in apoptosis vary, at least to some degree, depending on the cell type and death-inducing stimulus, all apoptotic cell death appears to undergo common terminal events including distinct morphological features of cytoplasmic shrinking, plasma membrane blebbing, condensation of nuclear chromatin, and fragmentation of genomic DNA. The apoptotic cells are eventually engulfed by neighboring cells or phagocytes, thereby avoiding an inflammatory response. Deshmukh et al., *Molec. Pharmac.* 51:897–906, 1997. Necrosis is a pathological type of cell death observed following physical or chemical injury, exposure to toxins, or ischemia and characterized by swelling, rupture of the plasma membrane and cellular organelles, and in vivo inflammation due to release of the cellular content into the surrounding tissue. Hengartner, M., in *Molecular Biology and Biotechnology*, Robert A. Myers, ed., VCH Publishers, Inc., 1995, p.158.

As demonstrated in the Examples below, p15 BID is produced by caspase cleavage of BID after the internal aspartic acid residue which corresponds to Asp60 and Asp59 of human and murine BID. As used herein, BID or p22 BID refers to the full-length BID polypeptide synthesized by a cell. Human and murine BID are 195 amino acids in length and it is believed that BID synthesized by other mammalian species is of similar length and can be identified by alignment with the human and murine BID amino acid sequences shown in FIG. 1.

Accordingly, one embodiment of the invention provides an isolated and purified polypeptide comprising a p15 BID polypeptide which has cell death agonist activity. As used herein, a p15 BID polypeptide contains the BH3 domain but lacks the N-terminal region of BID. Based on the conservation of the putative LQTD caspase recognition site in human and murine BID (see FIG. 4B), it is believed that BID proteins from other species, particularly mammalian species, are cleaved by a caspase after an aspailic acid corresponding to Asp60 and Asp59 of human and murine BID to produce p15 BID polypeptides having cell death agonist activity. Thus, p15 BID polypeptides embraced by the invention include any naturally-occurring p15 BID molecules as well as engineered p15 BID polypeptides comprising an amino acid sequence substantially identical to a naturally-occurring amino acid sequence.

By "substantially identical" is meant that two amino acid sequences of the same length share at least 85% sequence identity, preferably at least 90% sequence identity, more preferably at least 95% sequence identity or more. Preferably, amino acid positions which are not identical differ by conservative amino acid substitutions.

Conservative amino acid substitutions refer to the interchangeability of residues having similar side chains. Conservatively substituted amino acids can be grouped according to the chemical properties of their side chains. For example, one grouping of amino acids includes those amino acids that have neutral and hydrophobic side chains (A, V, L, I, P, W, F, and M); another grouping is those amino acids having neutral and polar side chains (G, S, T, Y, C, N, and Q); another grouping is those amino acids having basic side chains (K, R, and H); another grouping is those amino acids having acidic side chains (D and E); another grouping is those amino acids having aliphatic side chains (G, A, V, L, and I); another grouping is those amino acids having aliphatic-hydroxyl side chains (S and T); another grouping is those amino acids having amine-containing side chains (N, Q, K, R, and H); another grouping is those amino acids having aromatic side chains (F, Y, and W); and another grouping is those amino acids having sulfur-containing side chains (C and M). Preferred conservative amino acid substitutions groups are: R-K; E-D, Y-F, L-M; V-I, and Q-H.

It is also contemplated that a p15 BID polypeptide can comprise a modified amino acid or unusual amino acid at one or more positions in its amino acid sequence, and can also comprise amino acids that are glycosylated or phosphorylated so long as the p15 BID polypeptide has cell death agonist activity.

Preferred embodiments of the p15 BID polypeptide comprise SEQ ID NO:3 or SEQ ID NO:5 or conservatively substituted variants thereof. Even more preferably, the p15 BID polypeptide consists of SEQ ID NO:3.

The p15 BID polypeptides of the present invention can be made by recombinant DNA technology by expressing a nucleotide sequence encoding the desired amino acid sequence in a suitable transformed host cell. Using methods well known in the art, a polynucleotide encoding a p15 BID polypeptide may be operably linked to an expression vector, transformed into a host cell and culture conditions established that are suitable for expression of the p15 BID polypeptide by the transformed cell.

Any suitable expression vector may be employed to produce recombinant p15 BID polypeptides such as, for example, the mammalian expression vector pCB6 (Brewer, *Meth Cell Biol* 43:233–245, 1994) or the *E. coli* pET expression vectors, specifically, pET-30a (Studier et al., *Methods Enzymol* 185:60–89, 1990). Other suitable expression vectors for expression in mammalian and bacterial cells are known in the art as are expression vectors for use in yeast or insect cells. Baculovirus expression systems can also be employed.

A number of cell types may be suitable as host cells for expression of recombinant p15 BID polypeptides. Mammalian host cells include, but are not limited to, monkey COS cells, Chinese Hamster Ovary (CHO) cells, human kidney 293 cells, human epidermal A431 cells, human Colo 205 cells, 3T3 cells, CV-1 cells, other transformed primate cell lines, nonnal diploid cells, cell strains derived from in vitro culture of primary tissue, primary explants, HeLa cells, mouse L cells, BHK, HL-60, U937, HaK and Jurkat cells. Yeast strains that may act as suitable host cells include *Saccharomyces cerevisiae, Schizosaccharomyces pombe*, Kluyveromyces strains, Candida, and any other yeast strain capable of expressing heterologous proteins. Host bacterial strains include *Escherichia coli, Bacillus subtilis, Salmonella typhimurium* and any other yeast strain capable of expressing heterologous proteins. If the p15 BID polypeptide is made in yeast or bacteria, it may be necessary to modify the polypeptide, for example, by phosphorylation or glycosylation of the appropriate sites using known chemical or enzymatic methods, to obtain a biologically active p15 BID polypeptide.

The expressed p15 BID polypeptide can be isolated and purified using known purification procedures, such as gel filtration and ion exchange chromatography. As used herein, "isolated and purified" means that a designated polypeptide constitutes at least about 50 percent of a composition on a molar basis compared to total proteins or other macromolecular species present in the composition. Preferably, the polypeptide of the invention will constitute at least about 75 to about 80 mole percent of the total protein or other macromolecular species present. More preferably, an isolated and purified polypeptide will constitute about 85 to about 90 mole percent of a composition and still more preferably, at least about 95 mole percent or greater. Purification may also include affinity chromatography using an agent that will specifically bind the p15 BID polypeptide, such as a polyclonal or monoclonal antibody raised against BID or a C-terminal fragment thereof. Other affinity resins typically used in protein purification may also be used such as concanavalin A-agarose, HEPARIN-TOYOPEARL® (a heparin affinity resin) or CIBACROM BLUE 3GA SEPHAROSE® (a coenzyme analog agarose affinity resin). Purification of pBID polypeptides can also include one or more steps involving hydrophobic interaction chromatography using such resins as phenyl ether, butyl ether, or propyl ether.

It is also contemplated that a p15 BID polypeptide may be expressed as a fusion protein to facilitate purification. Such fusion proteins, for example, include a p15 BID polypeptide fused to a histidine tag such as when expressed in the pET bacterial expression system as well as a p15 BID polypeptide fused to maltose binding protein (MBP), glutathione-S-transferase (GST) or thioredoxin (TRX). Similarly, the polypeptide of the invention can be tagged with a heterologous epitope and subsequently purified by immunoaffinity chromatography using an antibody that specifically binds such epitope. Kits for expression and purification of such fusion proteins and tagged proteins are commercially available.

Alternatively, the p15 BID polypeptides of the invention may be produced by incubating BID, which has been isolated from cells or produced by recombinant DNA technology, with Caspase-8 or Caspase-3. In addition, p125 BID may be chemically synthesized using methods known to those skilled in the art.

Once prepared, the p15 BID polypeptide can be tested for cell death agonist activity using the assays described below or any known model of apoptotic and/or necrotic cell death.

In another embodiment, the present invention provides an isolated and purified polynucleotide comprising a nucleotide sequence that encodes a p15 BID polypeptide. As used herein, a polynucleotide includes DNA and/or RNA and thus the nucleotide sequences recited in the Sequence Listing as DNA sequences also include the identical RNA sequences with uracil substituted for thymine residues. Nucleotide sequences included in the invention are those encoding the p15 BID polypeptides set forth in SEQ ID NOS:3–5. It is understood by the skilled artisan that degenerate nucleotide sequences can encode the p15 BID polypeptides described herein and these are also intended to be included within the present invention. Such nucleotide sequences include modifications of naturally-occurring sequences in which at least one codon is substituted with a corresponding redundant codon preferred by a given host cell, such as E. coli or insect cells, so as to improve expression of recombinant p15 BID therein. Preferred polynucleotides of the invention encode human and mouse p15 BID as set forth in SEQ ID NO:3 and 5 and their nucleotide sequences can be determined by inspection of the known cDNA sequences for BID, see, e.g., copending application Ser. No. 08/706,741.

The present invention also encompasses vectors comprising an expression regulatory element operably linked to any of the p15 BID-encoding nucleotide sequences included within the scope of the invention. This invention also includes host cells, of any variety, that have been transformed with such vectors.

Also included in by the present invention are therapeutic or pharmaceutical compositions comprising a p15 BID polypeptide which cell death agonist activity and a method for promoting death of a target cell which comprises treating the cell with an effective amount of the p15 BID polypeptide.

As discussed in copending application Ser. No. 08/706, 741, mutations in the BID BH3 domain destroy its cell death agonist activity but not necessarily its ability to interact with other BCL-2 family members. Thus, it is believed that death of a target cell can be inhibited by treatment with a mutant p15 BID polypeptide lacking cell death agonist activity but retaining the ability to be translocated to the mitochondria or retaining the ability to competitively block translocation of p15 BID. Thus, other embodiments of the invention include therapeutic or pharmaceutical compositions comprising a mutant p15 BID polypeptide lacking cell death agonist activity and a method for inhibiting death of a target cell which comprises treating the cell with an effective amount of the mutant p15 BID polypeptide. The mutant p15 BID polypeptide is intended to be identical to a p15 BID polypeptide other than having an inactivating mutation in the BH3 domain that destroys its cell death agonist activity. It is also contemplated that the target cell can be treated with the mutant p15 BID polypeptide by delivering into the cell a mutant p22 BID polypeptide which is cleaved in the target cell by a caspase by a mechanism similar to or identical to that which produces p15 BID.

It is also contemplated that death of a target cell may be inhibited by treating the cell with a mutant p22 BID polypeptide that has a mutation in the p15 cleavage site which blocks cleavage of the mutant p22 BID at the cleavage site. By p15 cleavage site is meant a sequence of four contiguous amino acids in a BID protein which corresponds to the putative Caspase-8 LQTD recognition site in human and murine BID. A mutant BID containing an alanine substituted for the aspartic acid residue in this sequence is not cleaved at p15 when incubated in vitro with Caspase 8.

In the further description of the compositions and methods below the mutant p15 BID polypeptide and both types of mutant p22 BID polypeptides are intended to be included within the terms mutant BID or mutant BID polypeptide.

In some embodiments, cell death is promoted or inhibited by treating the target cell with a polynucleotide encoding p15 BID or mutant BID operably linked to a promoter that produces expression of p15 BID or mutant BID in the target cell. The polynucleotide can comprise an expression plasmid, a retrovirus vector, an adenovirus vector, an adenovirus associated vector (AAV) or other viral or nonviral vector used in the art to deliver genes into cells. Alternatively, the polynucleotide can be administered to the target cell by microinjection.

In embodiments where the target cell being treated is in a patient, such as cancer cells or virally-infected cells, the polynucleotide encoding p15 BID or mutant BID is administered to the patient. Any of the vectors discussed above, as well as nonviral methods such as lipid-based systems and polycation-based systems, can be used to administer the polynucleotide. It is also contemplated that the target cell may be treated with p15 BID or mutant BID by coinfection with a replication-defective adenovirus expressing p15 BID or mutant BID and another replication competent adenovirus that complements the replication defective virus to increase expression of the recombinant polypeptide in infected cells.

Preferably, the polynucleotide is selectively delivered to target cells within the patient so as not to affect viability of other tissues. Targeted delivery of the polynucleotide can be done for example by using delivery vehicles such as polycations, liposomes or viral vectors containing a targeting moiety that recognizes and binds to a specific marker on the target cell. Such methods are known in the art, see, e.g., U.S. Pat. No. 5,635,383. Another targeted delivery approach uses viral vectors that can only replicate in specific cell types which is accomplished by placing the viral genes necessary for replication under the transcriptional control of a response element for a transcription factor that is only active in the target cell. See, e.g., U.S. Pat. No. 5,698,443.

In other embodiments, the target cell is treated with a composition comprising a p15 BID polypeptide or a mutant BID polypeptide. Preferably, p15 BID or mutant BID is administered with a carrier that facilitates delivery of the polypeptide into the cell, such as liposomes. Where p15 BID or mutant BID is being administered to a patient, the liposomes can have targeting moieties exposed on the surface such as antibodies, ligands or receptors to specific cell surface molecules to limit delivery of p15 BID or mutant BID to targeted cells. Liposome drug delivery is known in the art (see, e.g., Amselem et al., *Chem. Phys. Lipid* 64:219–237, 1993). Alternatively, p15 BID or mutant BID can be modified to include a specific transit peptide that is capable of delivering the polypeptide into the cytoplasm of the target cell or the polypeptide can be delivered directly into a target cell by microinjection.

Compositions comprising a p15 BID polypeptide or a mutant BID polypeptide can be administered by any suitable route known in the art including, for example, intravenous, subcutaneous, intramuscular, transdermal, intrathecal or intracerebral or administration to cells in ex vivo treatment protocols. Administration can be either rapid as by injection or over a period of time as by slow infusion or administration of slow release formulation. For treating tissues in the central nervous system, administration can be by injection or infusion into the cerebrospinal fluid (CSF). The p15 BID polypeptide or mutant BID polypeptide can also be administered with one or more agents capable of promoting penetration of the polypeptide across the blood-brain barrier.

The p15 BID and mutant BID polypeptides can also be linked or conjugated with agents that provide desirable pharmaceutical or pharmacodynamic properties, including for example, substances known in the art to promote penetration or transport across the blood-brain barrier such as an antibody to the transferring receptor (Friden et al., *Science* 259:373–377, 1993), or a polymer such as polyethylene glycol to obtain desirable properties of solubility, stability, half-life and other pharmaceutically advantageous properties (Davis et al. *Enzyme Eng* 4:169–73, 1978; Burnham, *Am J Hosp Pharm* 51:210–218, 1994).

For nonparental administration, the compositions can also include absorption enhancers which increase the pore size of the mucosal membrane. Such absorption enhancers include sodium deoxycholate, sodium glycocholate, dimethyl-β- cyclodextrin, lauroyl-1-lysophosphatidylcholine and other substances having structural similarities to the phospholipid domains of the mucosal membrane.

The compositions are usually employed in the form of pharmaceutical preparations. Such preparations are made in a maimer well known in the pharmaceutical art. One preferred preparation utilizes a vehicle of physiological saline solution, but it is contemplated that other pharmaceutically acceptable carriers such as physiological concentrations of other non-toxic salts, five percent aqueous glucose solution, sterile water or the like may also be used. It may also be desirable that a suitable buffer be present in the composition. Such solutions can, if desired, be lyophilized and stored in a sterile ampoule ready for reconstitution by the addition of sterile water for ready injection. The primary solvent can be aqueous or alternatively non-aqueous.

The carrier can also contain other pharmaceutically-acceptable excipients for modifying or maintaining the pH, osmolarity, viscosity, clarity, color, sterility, stability, rate of dissolution, or odor of the formulation. Similarly, the carrier may contain still other pharmaceutically-acceptable excipients for modifying or maintaining release or absorption or penetration across the blood-brain barrier. Such excipients are those substances usually and customarily employed to formulate dosages for parenteral administration in either unit dosage or multi-dose form or for direct infusion by continuous or periodic infusion.

It is also contemplated that certain formulations comprising a p15 BID polypeptide or a mutant BID polypeptide are to be administered orally. Such formulations are preferably encapsulated and formulated with suitable carriers in solid dosage forms. Some examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, gelatin, syrup, methyl cellulose, methyl- and propylhydroxybenzoates, talc, magnesium, stearate, water, mineral oil, and the like. The formulations can additionally include lubricating agents, wetting agents, emulsifying and suspending agents, preserving agents, sweetening agents or flavoring agents. The compositions may be formulated so as to provide rapid, sustained, or delayed release of the active ingredients after administration to the patient by employing procedures well known in the art. The formulations can also contain substances that diminish proteolytic degradation and/or substances which promote absorption such as, for example, surface active agents.

The p15 BID polypeptide or mutant BID is administered to patients in an amount effective to promote death of target cells within the patient. The specific dose is calculated according to the approximate body weight or body surface area of the patient or the volume of body space to be occupied. The dose will also be calculated dependent upon the particular route of administration selected. Further refinement of the calculations necessary to determine the appropriate dosage for treatment is routinely made by those of ordinary skill in the art. Such calculations can be made without undue experimentation by one skilled in the art in light of the activity disclosed herein in cell death assays. Exact dosages are determined in conjunction with standard dose-response studies. It will be understood that the amount of the composition actually administered will be determined by a practitioner, in the light of the relevant circumstances including the condition or conditions to be treated, the choice of composition to be administered, the age, weight, and response of the individual patient, the severity of the patient's symptoms, and the chosen route of administration. Dose administration can be repeated depending upon the pharmacokinetic parameters of the dosage formulation and the route of administration used.

It is also contemplated that death of a target cell can be inhibited by treating the cell with a peptide which serves as a competitive inhibitor of p22 BID binding to Caspase-8. One such peptide comprises LQTD (SEQ ID NO:7). Peptide mimetics of LQTD are also contemplated and may be advantageous to improve stability, binding affinity and other characteristics. The design and synthesis of peptide mimetics are well known in the art. Administration and dosage of caspase-cleavage blocking peptides and peptide mimetics can be accomplished using the detailed descriptions above.

Preferred embodiments of the invention have been described above. Other embodiments within the scope of the claims herein will be apparent to one skilled in the art from consideration of the specification and the examples below or by practice of the invention as disclosed herein. It is intended that the specification, together with the Examples, be considered exemplary only, with the scope and spirit of the invention being indicated by the claims which follow below.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

All references cited in this specification are hereby incorporated by reference. The discussion of references herein is intended merely to summarize the assertions made by their authors and no admission is made that any reference constitutes prior art. Applicants reserve the right to challenge the accuracy and pertinency of the cited references.

The following materials and methods were used in the examples, unless otherwise noted:

TNF/Chx Treatment and Western Blot Analysis

Cells were treated with recombinant mouse TNF-α (1 ng/ml; Sigma) and cycloheximide (1 $\mu$g/ml; Sigma), and lysed at the indicated times in 50 mM Tris (pH 7.5), 150 mM NaCl, 1% Triton X-100 supplemented with a protease inhibitor cocktail (Sigma; added at a 1:100 dilution). Lysates were separated by SDS-PAGE, and transferred to a polyvinylidine difluoride (PVDF; Bio-Rad) membrane. The membrane was first blocked with 5% milk for 1 hr., followed by incubation with primary and secondary Abs for 1 hr. each, and finally developed with enhanced chemiluminescence (Amersham). A rabbit anti-mouse BID polyclonal Ab (Wang et al., 1996) was used at 1:1000 dilution, anti-cytochrome c mAb (PharMingen) was used at 1:500 dilution and anti-cytochrome c oxidase subunit IV Ab was used at 1:1000 dilution. The HRPO-conjugated secondary Abs (Caltag) were used at 1:2000 dilution.

Viability, Mitochondrial Potential and Reactive Oxygen Species (ROS) Measurement Viability was determined at designated time points by propidium iodide (PI) dye exclusion. For mitochondrial potential and intracellular ROS production, $5 \times 10^5$ cells were incubated for 15 min. at 37° C. with 3,3'-dihexyloxacarbocynine iodide [DiOC$_6$(3), 40 nM] or hydroethidine (2 $\mu$M; Molecular Probes) followed by FACScan (Becton Dickinson) analysis.

Recombinant BID Preparation and Purification

Murine BID was cloned into pGEX-KG. GST-BID fusion protein was induced in BL21DE3 by 1 mM IPTG. The bacterial pellet was resuspended in lysis buffer (1% Triton X-100; 1 mM EDTA, 1 mM DTT in PBS) supplemented with a protease inhibitor cocktail (Sigma; added at a 1:100 dilution), and sonicated. After centrifugation at 10,000 g for 20 min., the supernatant was applied to glutathioneagarose beads (Sigma). The beads were washed with buffer and treated with 10 units of thrombin per original liter. Cleaved BID was eluted from beads and the cleavage reaction was terminated by adding 50 µg/ml of Nα-p-tosyl-L-lysine chloromethyl ketone (TLCK). To remove the GST protein and incompletely cleaved fusion proteins, the preparation was further purified on MONOQ ion exchange column and the proteins were eluted with a NaCl gradient.

Cleavage of BID and N-terminal Sequence Analysis

Recombinant BID (5 µg) was incubated for 2 hrs. at 37° C. with the soluble fraction of FL5.12 cells pretreated with TNF/Chx for 5 hrs. The proteins were lysed, separated by 16% SDS-PAGE and transferred to a polyvinylidine difluoride (PVDF; Bio-Rad) membrane. The membrane was first stained with Coomasie blue and then destained with 80% methanol. The desired protein bands were cut out and subjected to N-terminal Edman degradation (Tempst et al., 1994).

Subcellular Fractionation

FL5.12 cells were washed once in phosphate-buffered saline (PBS), resuspended in isotonic HIM buffer (200 mM mannitol, 70 mM sucrose, 1 mM EGTA, 10 mM HEPES, pH 7.5) supplemented with a protease inhibitor cocktail (Sigma; added at a 1:100 dilution), and homogenized using a polytron homogenizer (Brinkmann Instruments) at setting 6.5 for 10 sec. Nuclei and unbroken cells were separated at 120 g for 5 min. as the low speed pellet (P1). This supernatant was centrifuged at 10,000 g for 10 min. to collect the heavy membrane pellet (HM). This supernatant was centrifuged at 100,000 g for 30 min. to yield the light membrane pellet (LM) and final soluble fraction (S). For subcellular fractionation of mouse hepatocytes, cells were homogenized and separated by differential centrifugation as described below for preparation of mitochondria from mouse liver.

Mitochondria from Mouse Liver

For isolation of intact mitochondria, the liver from one mouse was minced and washed in ice-cold HIM buffer (supplemented with 2 mg/ml de-lipidated BSA). The minced liver (~2 g wet weight) was gently homogenized in 6 ml HIM buffer in a 15-ml Wheaten Dounce glass homogenizer using two complete up and down cycles of a glass 'B'-type pestle. The homogenate was diluted 6-fold with HIM buffer and centrifuged at 4° C. for 10 min. at 600 g in a sorval SS34 rotor. The supernatant was recovered, centrifuged at 7000 g for 15 min. and the pellet resuspended in twice the original homogenate volume in HIM buffer w/o BSA. After centrifuging at 600 g, mitochondria were recovered from the supernatant by centrifuging at 7000 g for 15 min. The mitochondrial pellet was suspended in 0.5 ml MRM buffer (250 mM sucrose, 10 mM HEPES, 1 mM ATP, 5 mM NaSuccinate, 0.08 mM ADP, 2 mM $K_2HPO_4$, pH 7.5) at a concentration of I mg of mitochondrial protein per ml, and adjusted to 1 mM DTT just before use (McBride et al., 1995).

Protein Import

For a standard import reaction, 60 µl of the soluble fraction of FL5.12 cells or epatocytcs was incubated with 10 µl of mitochondria in MRM buffer (1 mg protein/ml) at 37° C. for 30 min. This import reaction was centrifuged at 10,000 g for 10 min. to pellet the mitochondria. Both the pellet and the supernatant were analyzed y Western blot. For alkali extraction, the mitochondrial pellet was resuspended in freshly prepared 0.1 M $Na_2CO_3$, pH 11.5, and incubated for 30 min. on ice. The membranes were subsequently pelleted in an ultracentrifuge (Beckman) at 75,000 g for 10 min. and both the pellet and the supernatant were analyzed by Western blot. For the BID depletion experiments, the soluble fraction of FL5.12 cells was incubated with anti-BID Ab for 1.5 hrs. on ice. The Ab complexes were captured with protein A beads for 1 hr. and removed by centrifugation, and the procedure was repeated. The resulting BID-depleted supernatant was used in the protein import reaction. For the recombinant caspase experiments, the soluble fraction of FL5.12 cells was incubated with recombinant caspase-8 or-3 (1 µg/60 µl; PharMingen) at 37° C. for 1 hr. and then used in the protein import reaction.

Anti-Fas Antibody Injection

6–8-week-old (20 g) C57B16 mice were injected intravenously with 5 µg of purified hamster monoclonal antibody to mouse Fas (JO2; PharMingen) in 100 µl of 0.9% w/v saline. Animals were sacrificed at the indicated times.

EXAMPLE 1

This example illustrates that cell death induced by TNFα/cycloheximide treatment includes mitochondrial dysfunction and caspase-mediated cleavage of BID.

As part of an assessment of the effects of death stimuli on the subcellular localization and post-translational modification of BCL-2 family members, the response of the early hernatopoietic cell line FL5.12 to TNFα was examined. Most non-transformed cells are resistant to TNF unless treated with a protein synthesis inhibitor (e.g. cycloheximide) which presumably eliminates a short half-life survival molecule (Polunovsky et al., *Exp. Cell Res.* 214:584–594, 1994).

Treatment of FL5.12 with a combination of TNFα/cycloheximide (TNF/Chx) resulted in a rapid reduction in the mitochondrial transmembrane potential as assessed by the cationic, lipophilic dye dihexyloxacarbocynine iodide [$DiOC_6(3)$] (FIG. 3A). The production of reactive oxygen species (ROS) such as superoxide as measured by conversion of hydroethidine to ethidium (HE) and cell death as determined by propidium iodide (PI) dye exclusion, followed closely (FIG. 3A). Both the mitochondrial dysfunction and cell death were blocked by pre-treatment with the broad caspase inhibitor, zVAD-fmk (FIG. 3A).

Figure 3B:
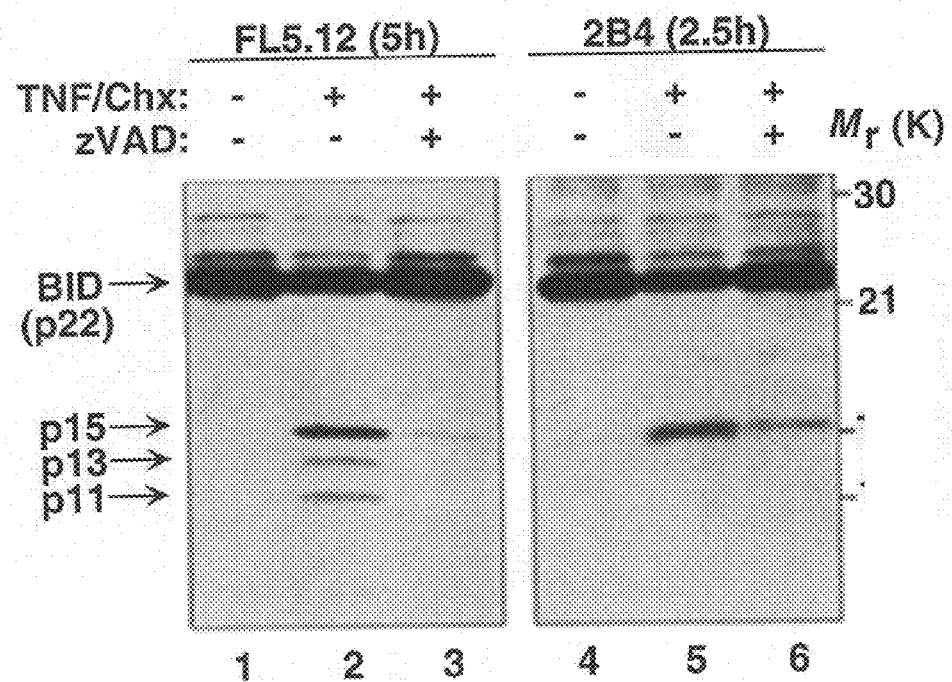
FIG. 3B is a digitized image of proteins from whole cell lysates of FL5.12 cells or 2B4 cells treated with TNFα/Chx in the presence or absence of zVAD-fmk which were fractionated by SDS-PAGE and analyzed by Western blot with anti-BID Ab.

Western blot analysis of whole cell lysates prepared from FL5.12 cells treated with TNF/Chx revealed that the intracellular pro-apoptotic molecule p22 BID was cleaved to yield a major p15 and minor p13 and p11 fragments (FIG. 3B). The 2B4 T cell hybridoma which is also killed by TNF and displays mitochondrial dysfunction (data not shown) also demonstrated the p15 fragment (FIG. 3B). Pre-treatment of cells with 50 µM zVAD-fmk markedly inhibited BID cleavage in FL5.12 cells and to a large extent in 2B4 cells (FIG. 3B).

EXAMPLE 2

This example illustrates that BID is cleaved at three internal aspartic acid residues.

Figure 4A:
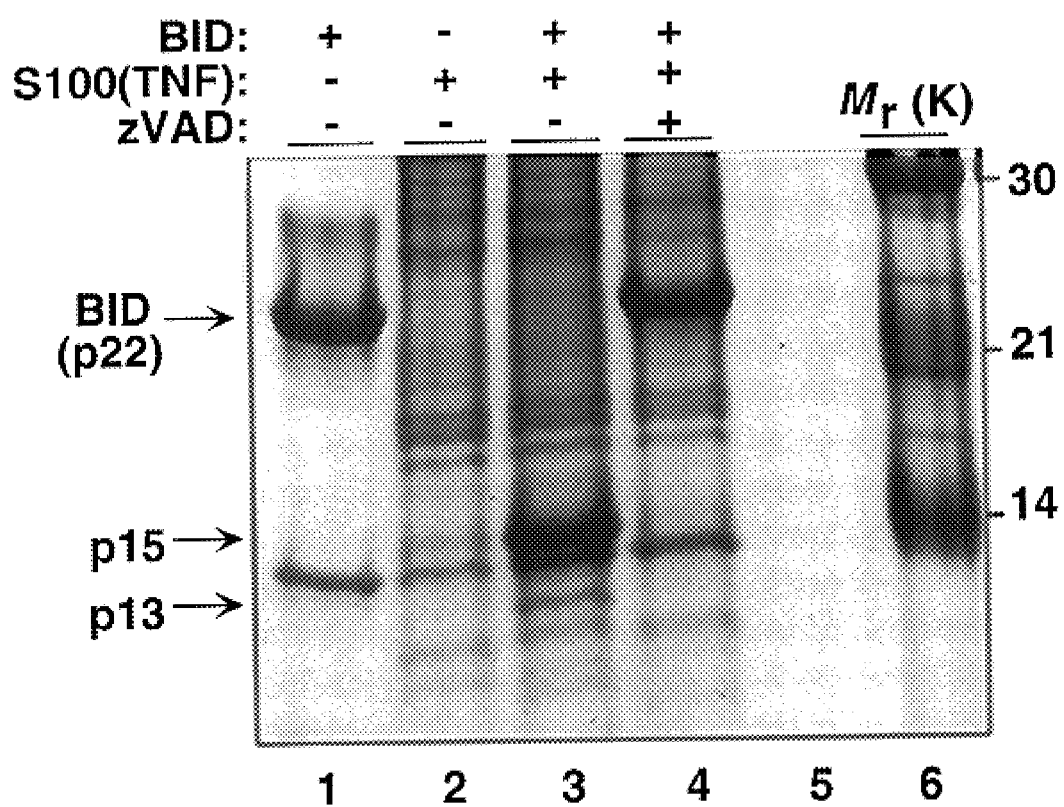
FIG. 4A is a digitized image of a Western blot of murine BID incubated with the cytosol of FL5.12 cells treated with TNFα/Chx (S100(TNF)) in the presence or absence of zVAD-fmk.
Figure 4B:
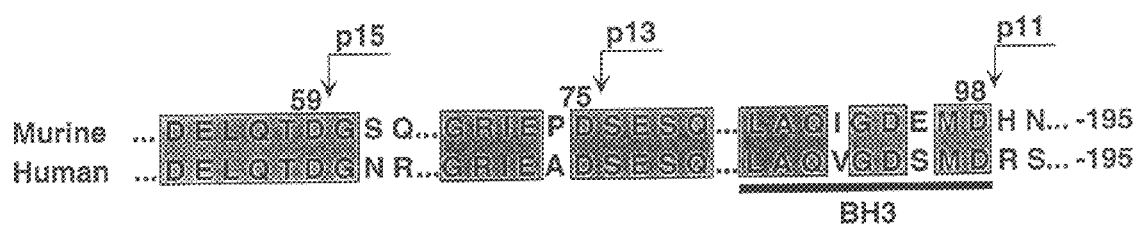
FIG. 4B shows aligned partial sequences of murine and human BID showing the caspase cleavage sites in murine BID.

To determine the cleavage sites in BID, recombinant murine BID (rBID) was incubated for 2 hrs. at 37° C. with the S100 fraction of TNF/Chx treated FL5.12 cells, S100 (TNF) (FIG. 4A). Following the reaction, the mixture was size fractionated by polyacrylamide gel electrophoresis (SDS-PAGE) followed by coomasie blue staining. The S100 (TNF) caused complete cleavage of p22 rBID (lane 3) which was inhibited by the inclusion of 50 μM zVAD-fmk in the reaction mixture (lane 4). p22 rBID cleavage generated a major p15 and minor p13 fragment. Incubation of rBID with either recombinant active Caspase-8 or Caspase-3 also generated the p15 fragment (not shown). N-terminal peptide sequence analysis of these fragments revealed that p22 rBID was cleaved between amino-acids Asp59-Gly60 to generate p15 and between amino-acids Asp75-Ser76 to generate the p13 fragment (FIG. 4B). These fragments comigrated precisely with the upper two fragments detected in TNF treated cells (FIG. 3B and data not shown), arguing that intracellular BID is also cleaved at these sites.

To determine whether the third cleavage site responsible for the less abundant p11 seen in FL5.12 cells (FIG. 3B) was the predicted Asp98 residue an Asp98Ala mutant was utilized. $^{35}$S-labeled in-vitro translated (IVT) BID and BID (D98A) were incubated with S100(TNF) from FL5.12 cells and analyzed by SDS-PAGE. Cleavage of wild type BID generated the three cleavage products seen in vivo, whereas cleavage of BID(D89A) generated only the p15 and p13 fragments (not shown). Taken together, BID is cleaved after three Asp residues located at position 59, 75 or 98 generating three fragments (p15,p13, and p11)(FIG. 4B).

EXAMPLE 3

This example illustrates that TNF/Chx treatment leads to accumulation of p15 BID in mitochondria as an integral membrane protein and release of cytochrome c.

Figure 5A:
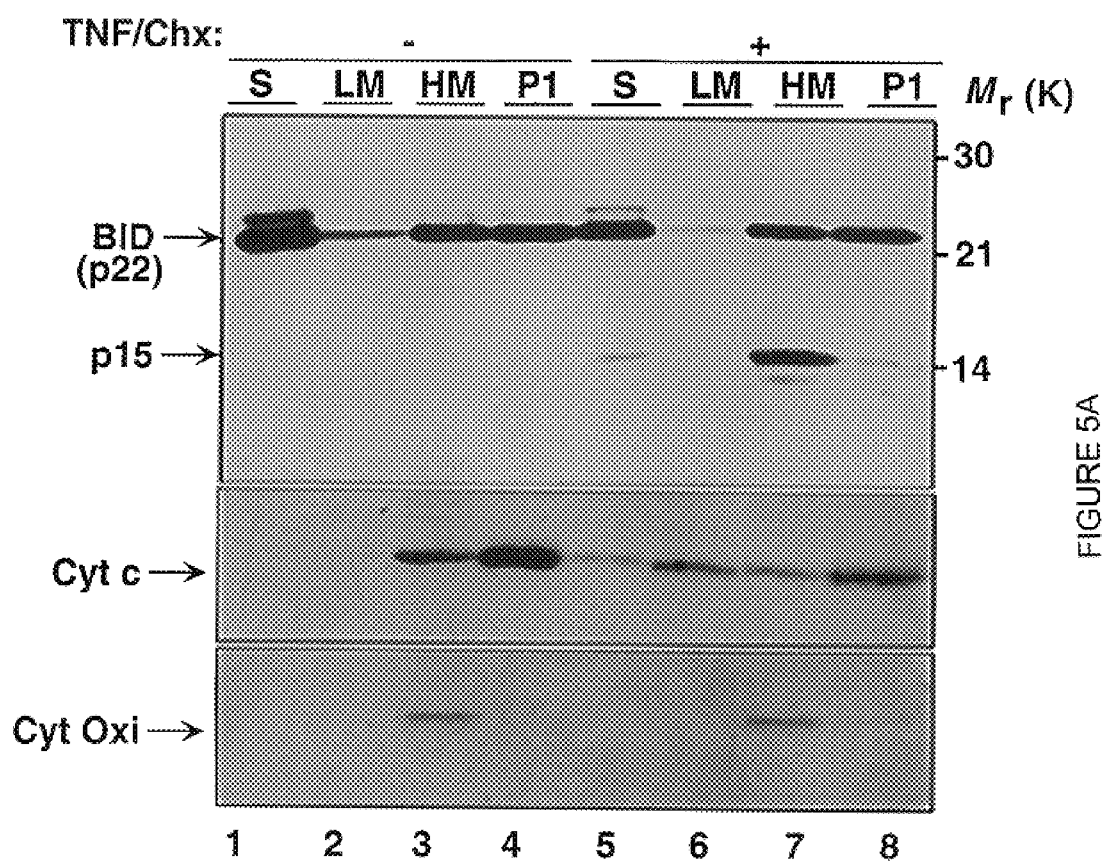
FIG. 5A is a digitized image of a Western blot of BID, cytochrome c (Cyt c), and anticytochrome c oxidase subunit IV (Cyt oxi) detected in various subcellular fractions using appropriate antibodies.

To assess the location of intracellular BID, FL5.12 cells were disrupted using isotonic lysis conditions which kept mitochondria intact with a retained outer membrane. A substantial portion of p22 BID was consistently in the soluble S100 fraction (S) representing the cytosol as well as the mitochondria-enriched heavy membrane (HM) fraction as documented by the mitochondrial markers (cytochrome c, intermembrane space; cytochrome c oxidase, inner membrane) (FIG. 5A, lanes 1–4). The low speed pellet (P1) comprised of residual whole cells, nuclei and some mitochondria, also displays BID.

At 5 hrs. following TNF/Chx treatment the p15 BID fragment was often still present in the cytosol but was predominantly in the mitochondrial HM fraction, (FIG. 5A, lanes 5–8). By 7 hrs. p15 BID was almost exclusively in the mitochondria. The p13 and p11 minor fragments were associated exclusively with the mitochondrial fraction (not shown). In addition, following the TNF/Chx death stimulus, most of the cytochrome c was released from the mitochondrial HM fraction, found either in the S100 fraction or presumably as part of membrane fragments in the LM fraction (FIG. 5A, middle panel).

Figure 5B:
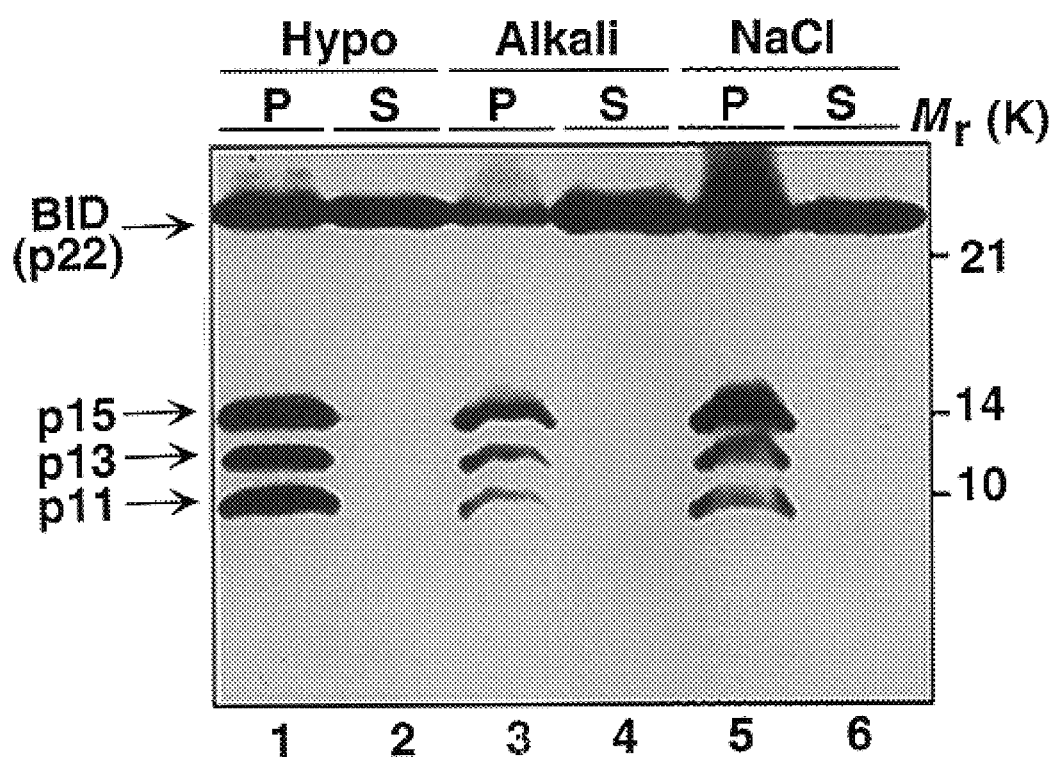
FIG. 5B is a digitized image of a Western blot showing that BID cleavage products in mitochondria are resistant to alkali and salt extraction.

To assess the membrane association of p22 BID and its cleavage products, the mitochondria (HM fraction) from TNF/Chx treated FL5.12 cells were incubated in hypotonic buffer, alkaline buffer or in high salt. The mitochondrial pellet (P) was separated from the supernatant (S) by high speed centrifugation. p22 BID was sensitive to all three treatments (>50% found in the supernatant (FIG. 5B)); whereas, p15, p13 and p11 were markedly resistant to these treatments (FIG. 5B) indicative of an integral membrane position.

EXAMPLE 4

This example illustrates that cytosolic p15 BID targets mouse liver mitochondria while p22 BID does not.

To assess whether the p15 BID fragment can target mitochondria, the cytosol of FL5.12 cells 5 hrs. after TNF/Chx treatment, S100(TNF)(FIG. 5C, lane 2) was incubated with purified, intact mitochondria from mouse liver (FIG. 5C, lane 1) in a standard protein import reaction. At 37° C.>90% of p15 BID but <10% of p22 BID targeted mitochondria (FIG. 5C, lanes 3,4). Moreover, the targeted p15 but not p22 was resistant to alkali extraction (lanes 9–12), indicating that p15 BID was now an integral membrane protein. Targeting of p15 BID did not occur at 4° C. (lanes 5,6). Moreover, the inclusion of zVAD-fmk in the reaction did not inhibit targeting of pre-existing p15 (lanes 7,8) arguing that this event does not require an additional caspase cleavage at the mitochondria.

EXAMPLE 5

This example illustrates that targeting of cytosolic p15 BID to mitochondria is required for the release of cytochrome c.

Figure 6A:
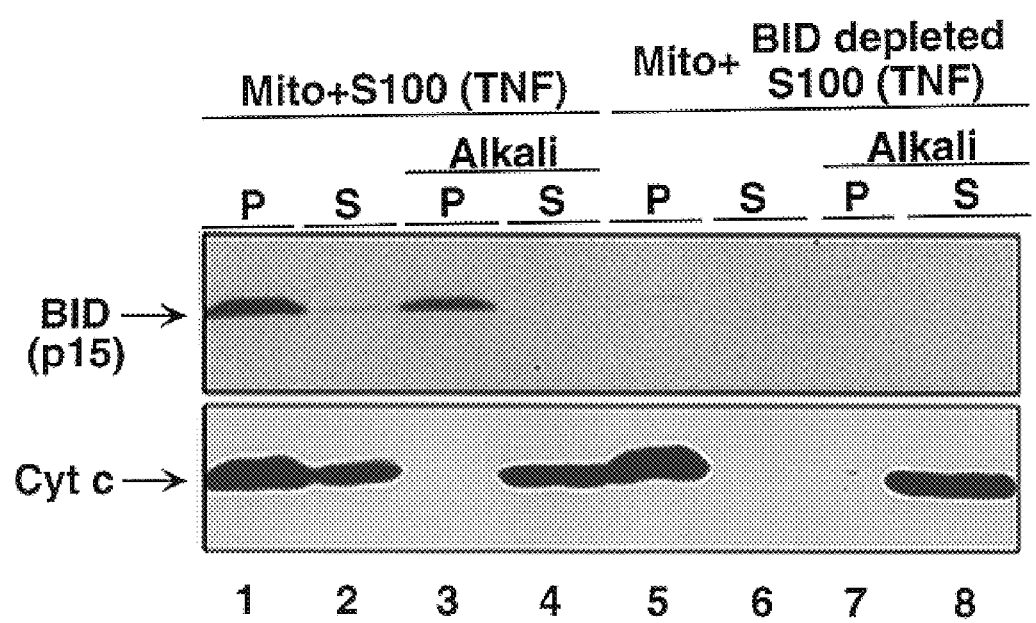

The cleavage of cytosolic BID by TNF-induced caspases and the targeting of p15 BID to the mitochondria represents an attractive correlate with the mitochondrial dysfunction/ cytochrome c release. It was then decided to determine if the targeting of p15 to mitochondria is in and of itself required for the release of cytochrome c. When the cytosol of TNF/Chx treated cells, S100(TNF), was incubated with mouse liver mitochondria for 30 min. at 37° C., p15 BID targeted mitochondria and up to ~50% of cytochrome c was released into the supernatant (FIG. 6A, lanes 1,2). p15 BID was resistant to alkali extraction whereas as expected cytochrome c was not (lanes 3,4). Strikingly, depletion of p15 BID from the S100(TNF) by an anti-BID Ab which eliminated p15 targeting also prevented the release of cytochrome c (lanes 5–8).

EXAMPLE 6

This example illustrates that BID is the required substrate of recombinant caspases responsible for the release of cytochrome c.

Figure 6B:
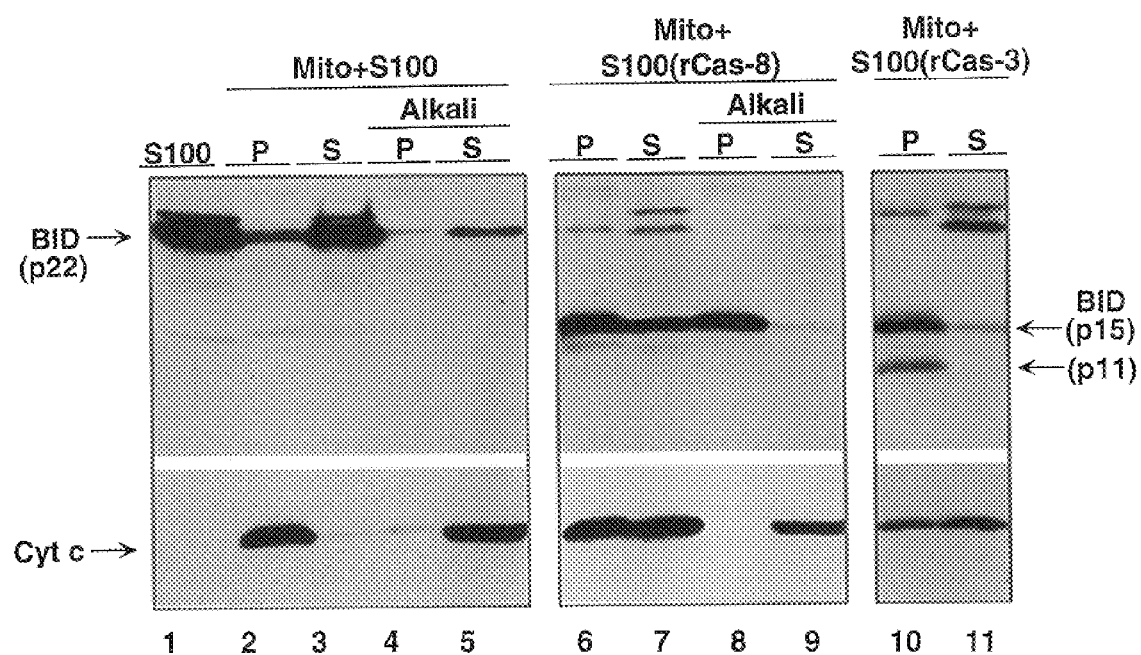

Next to be determined was whether BID is also a required substrate that must be cleaved by caspases in order for cytochrome c to be released. In this paradigm, a soluble fraction (S100) from untreated FL5.12 cells was preincubated with recombinant Caspase-8 or Caspasc-3 (rCas-8,-3) and then added to mouse liver mitochondria. When either the S100 fraction or recombinant Caspases were incubated separately with mitochondria there was no release of cytochrome c (FIG. 6B, lanes 2,3 and data not shown). However, addition of active rCas-8 to the S100 generated p15 BID (lanes 6,7), while addition of rCas-3 generated both p15 and p11 BID (lanes 10,11). In both instances, the BID fragments targeted mitochondria as integral membrane proteins (lanes 8,9 and data not shown) and ~50% of cytochrome c was released (lower panel, lanes 6,7,10,11). Once again, immunodepletion of p15 BID from the S100(rCas-8) prevented the release of cytochrome c when this activated cytosol was added to mitochondria (FIG. 6C, lanes 3,4).

EXAMPLE 7

This example illustrates that anti-Fas Ab injection of mice results in accumulation of p15 BID in the cytosol of hepatocytes and its subsequent translocation to mitochondria.

Figure 7A:
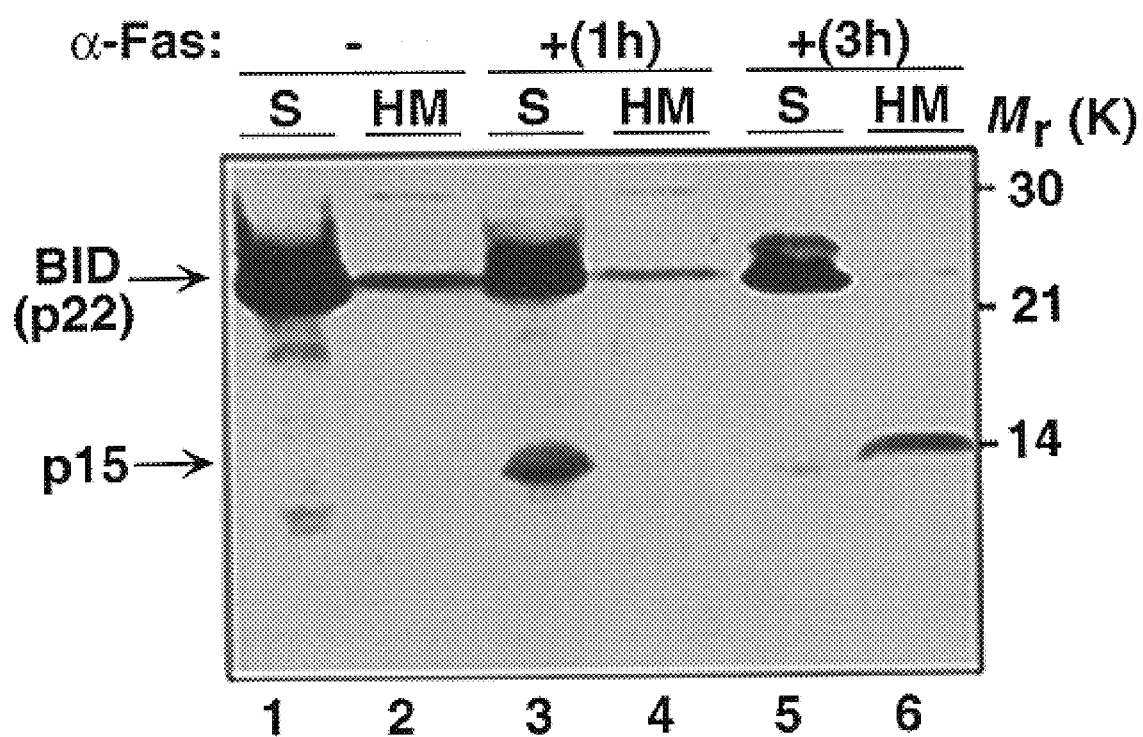
FIGS. 7A–7C are digitized images of Western blots showing that anti-Fas Ab injection of mice results in accumulation of p15 BID in the cytosol of hepatocytes and is subsequently translocated to mitochondria.
Figure 7B:
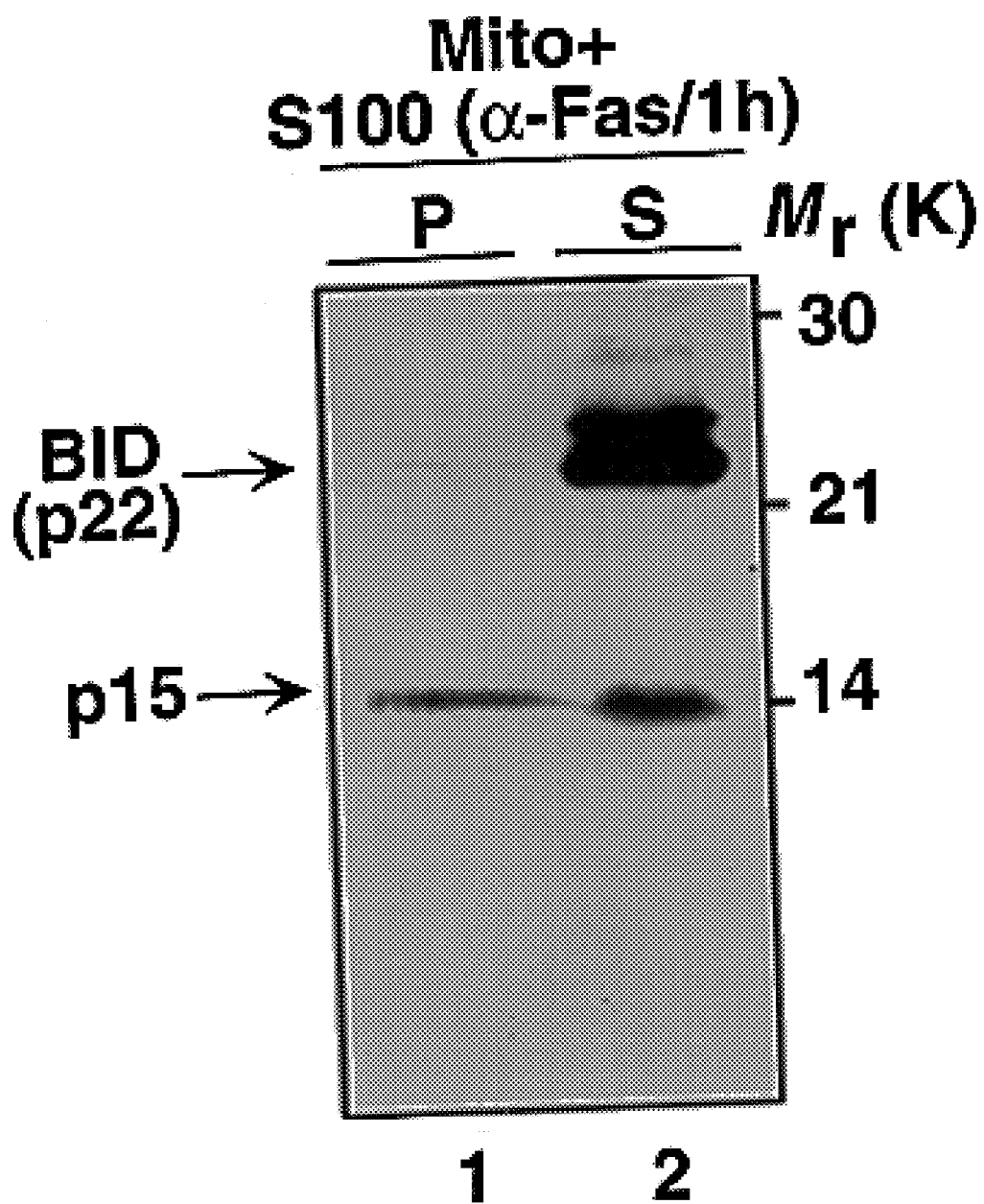
Figure 7C:
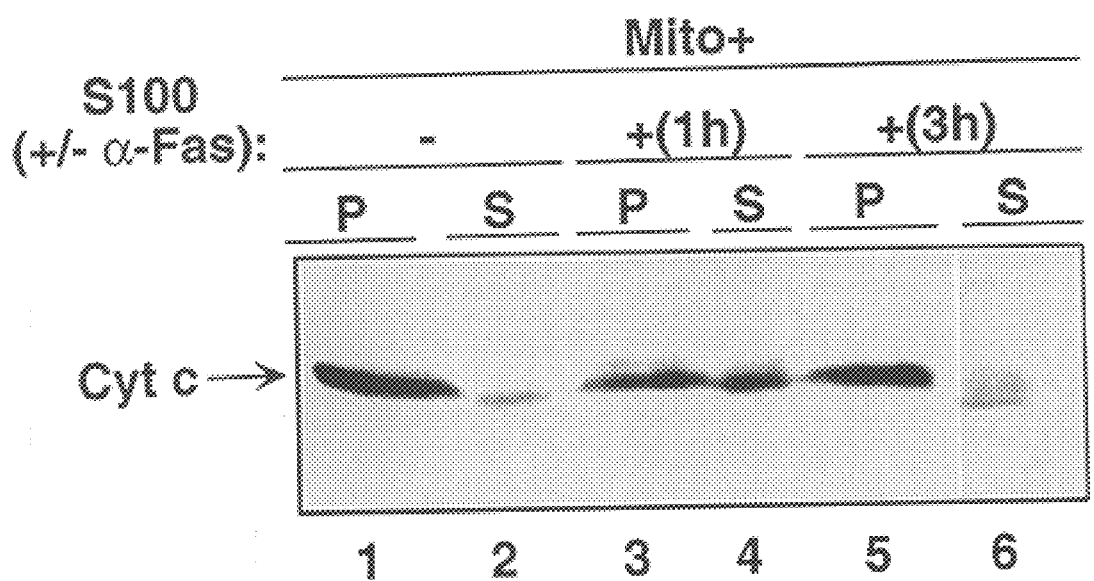

To assess the involvement of BID in the TNF/Fas death pathway in-vivo, mice were injected with anti-Fas Ab which results in massive hepatocyte cell death. To determine the subcellular location of BID, we disrupted hepatocytes using isotonic lysis conditions which kept their mitochondria intact with a retained outer membrane. The p22 BID in normal, untreated hepatocytes was predominantly in the cytosolic (S) fraction (FIG. 7A, lanes 1,2). However, by 1 hr. following anti-Fas Ab injection p15 BID appeared in the soluble S100 fraction (S) (FIG. 7A, lanes 3,4). Of note by 3 hrs. following Ab injection p15 was associated exclusively with the mitochondrial fraction (HM) (FIG. 7A, lanes 5,6). In addition, the p15 but not p22 BID from the liver cytosol of mice treated for 1 hr. with anti-Fas Ab was capable of targeting mitochondria in-vitro (FIG. 7B). Moreover, that same cytosol that possessed p15 at 1 hr. post-treatment released cytochrome c from mitochondria (FIG. 7C, lanes 3,4). However, the cytosolic fraction from hepatocytes 3 hrs. post treatment, which no longer had p15 BID present (FIG. 7A, lane 5), did not release cytochrome c substantially (FIG. 7C, lanes 5,6).

Discussion

Figure 8:
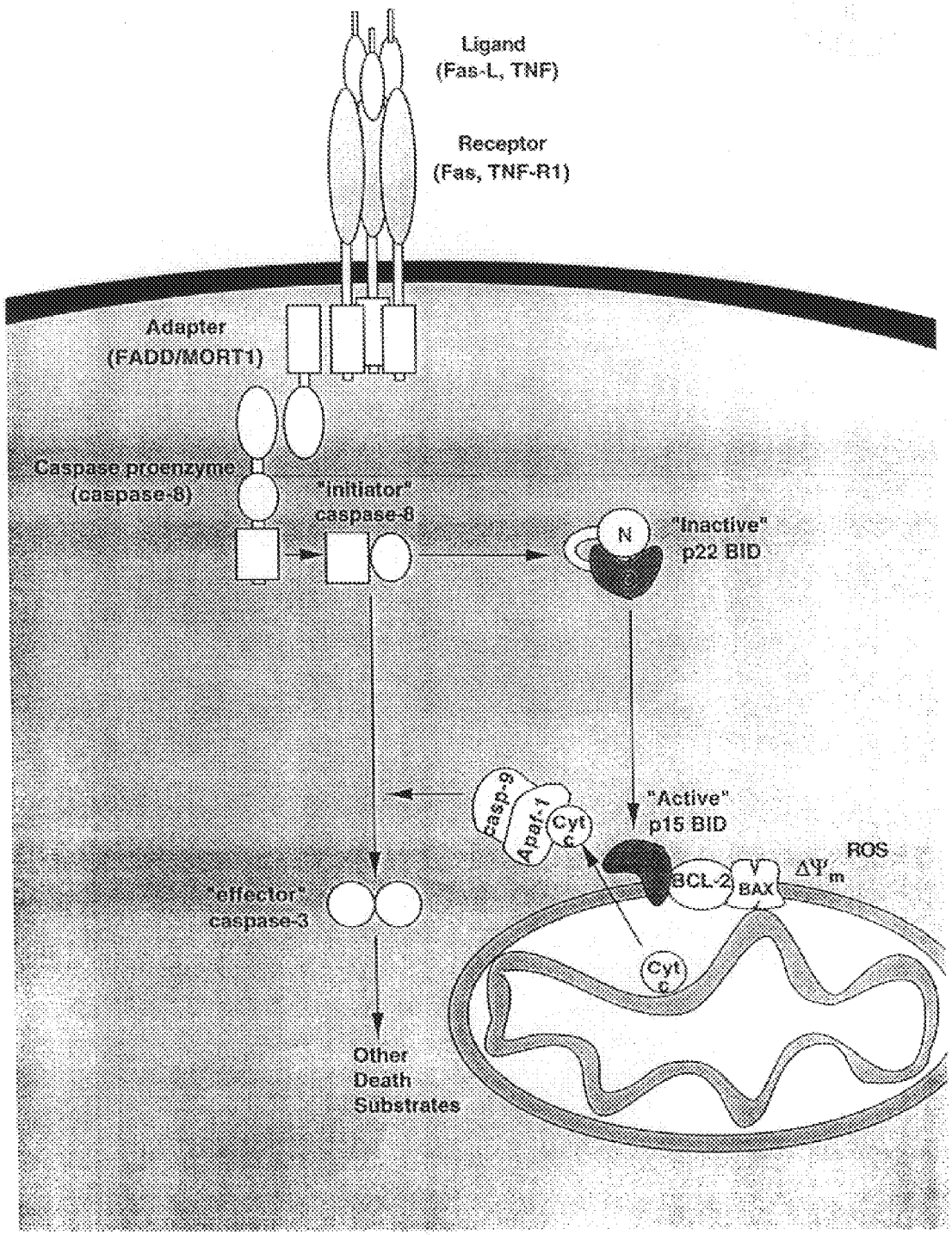
FIG. 8 is a model of BID cleavage and translocation following TNF receptor/Fas engagement.

These data indicate that the TNF and Fas death signal pathways converge at BID, a shared pro-apoptotic effector belonging to the "BH3 domain only" subset of the BCL-2 family. Our studies suggest a model in which cytosolic p22 BID represents an inactive conformation of the molecule that is proteolytically cleaved to generate an active p15 BID (FIG. 8). In retrospect, this may account for the greater protection by caspase inhibitors of BID-induced death (Wang et al., 1996) compared to BAX-induced death (Xiang et al., 1996). The p 1 5 conformation rather selectively targets mitochondria where it resides as an integral membrane protein responsible for the release of cytochrome c (FIG. 8). Caspase-8 presumably directly cleaves BID following its own activation by TNF-R/Fas engagement as Caspase-8 prefers the D59 site of BID. Removal of the $NH_2$-terminus would retain and potentially expose the predicted amphipathic α helix, BH3, on the active COOH-terminal p15 fragment. This proteolytic cleavage may alter an inert, intramolecular folded BID or alternatively release BID from a tethering chaperone-like molecule. Immunodepletion of p15 BID from cytosols activated by either TNF-R engagement or Caspase-8 addition indicates that p15 BID is requisite for the release of cytochrome c from mitochondria.

Intracellular p22 BID was cleaved at three internal Asp sites: D59, D75 and D98 (FIG. 4B). Of note the minor fragments of p13 and p11 resulting from cleavage at D75 and D98 respectively, are only detected in the mitochondria. While Caspase-8 prefers the D59 site, other caspases perhaps at the level of mitochondria may be responsible for the p13 and p11 fragments. The p11 fragment was not observed in mitochondria protected by BCL-$X_L$ lending support to this thesis. These smaller fragments appear of less certain importance as they are not prominent in TNF-activated 2B4 cells or Fas-activated hepatocytes. The LQTD↓ recognition motif for the predominant p15 fragment is an atypical site for "initiator" caspases (6,8,9; (I/L/V)EXD). The DEMD↓ motif which was recognized by recombinant caspase-3 is a classic site for "effector" caspases (2,3,7; DEXD). Of note all three recognition sites are well conserved between mouse and human BID (FIG. 4B). Caspase cleavage of BCL-2 (Cheng et al., 1997) and BCL-$X_L$ (Clem et al., 1998) have been reported which convert them from anti- to pro-apoptotic molecules. Thus, caspase cleavage of the BCL-2 members may represent a feed forward loop to insure cell death.

What is claimed is:

1. An isolated and purified BID polypeptide fragment comprising a p15 BID polypeptide which has cell death activity wherein said fragment does not include full-length BID.

2. The isolated and purified BID polypeptide fragment of claim 1, comprising SEQ ID NO:3, SEQ ID NO:4, or SEQ ID NO:5.

3. The isolated and purified polypeptide of claim 1, consisting of SEQ ID NO:3, SEQ ID NO:4, or SEQ ID NO:5.

4. A composition for promoting death of a target cell which comprises the BID polypeptide fragment of claim 1 and a carrier suitable for facilitating delivery of the BID polypeptide fragment into the cell.

5. The composition of claim 4, wherein the BID polypeptide fragment comprises SEQ ID NO:3, SEQ ID NO:4, or SEQ ID NO:5.

6. The composition of claim 4, wherein the BID polypeptide fragment consists of SEQ ID NO:3, SEQ ID NO:4, or SEQ ID NO:5.

* * * * *

SEQUENCE LISTING

<160> NUMBER OF SEQ ID NOS: 7

<210> SEQ ID NO 1
<211> LENGTH: 195
<212> TYPE: PRT
<213> ORGANISM: Homo sapiens

<400> SEQUENCE: 1

```
Met Asp Cys Glu Val Asn Asn Gly Ser Ser Leu Arg Asp Glu Cys Ile
 1               5                  10                  15

Thr Asn Leu Leu Val Phe Gly Phe Leu Gln Ser Cys Ser Asp Asn Ser
            20                  25                  30

Phe Arg Arg Glu Leu Asp Ala Leu Gly His Glu Leu Pro Val Leu Ala
        35                  40                  45

Pro Gln Trp Glu Gly Tyr Asp Glu Leu Gln Thr Asp Gly Asn Arg Ser
    50                  55                  60

Ser His Ser Arg Leu Gly Arg Ile Glu Ala Asp Ser Glu Ser Gln Glu
65                  70                  75                  80

Asp Ile Ile Arg Asn Ile Ala Arg His Leu Ala Gln Val Gly Asp Ser
                85                  90                  95

Met Asp Arg Ser Ile Pro Pro Gly Leu Val Asn Gly Leu Ala Leu Gln
            100                 105                 110

Leu Arg Asn Thr Ser Arg Ser Glu Glu Asp Arg Asn Arg Asp Leu Ala
        115                 120                 125

Thr Ala Leu Glu Gln Leu Leu Gln Ala Tyr Pro Arg Asp Met Glu Lys
```

```
                130             135             140
Glu Lys Thr Met Leu Val Leu Ala Leu Leu Ala Lys Lys Val Ala
145                 150                 155                 160

Ser His Thr Pro Ser Leu Leu Arg Asp Val Phe His Thr Thr Val Asn
                165                 170                 175

Phe Ile Asn Gln Asn Leu Arg Thr Tyr Val Arg Ser Leu Ala Arg Asn
                180                 185                 190

Gly Met Asp
        195

<210> SEQ ID NO 2
<211> LENGTH: 195
<212> TYPE: PRT
<213> ORGANISM: Mus musculus

<400> SEQUENCE: 2

Met Asp Ser Glu Val Ser Asn Gly Ser Gly Leu Gly Ala Lys His Ile
  1               5                  10                  15

Thr Asp Leu Leu Val Phe Gly Phe Leu Gln Ser Ser Gly Cys Thr Arg
                 20                  25                  30

Gln Glu Leu Glu Val Leu Gly Arg Glu Leu Pro Val Gln Ala Tyr Trp
             35                  40                  45

Glu Ala Asp Leu Glu Asp Glu Leu Gln Thr Asp Gly Ser Gln Ala Ser
     50                  55                  60

Arg Ser Phe Asn Gln Gly Arg Ile Glu Pro Asp Ser Glu Ser Gln Glu
 65                  70                  75                  80

Glu Ile Ile His Asn Ile Ala Arg His Leu Ala Gln Ile Gly Asp Glu
                 85                  90                  95

Met Asp His Asn Ile Gln Pro Thr Leu Val Arg Gln Leu Ala Ala Gln
                100                 105                 110

Phe Met Asn Gly Ser Leu Ser Glu Asp Lys Arg Asn Cys Leu Ala
             115                 120                 125

Lys Ala Leu Asp Glu Val Lys Thr Ala Phe Pro Arg Asp Met Glu Asn
130                 135                 140

Asp Lys Ala Met Leu Ile Met Thr Met Leu Leu Ala Lys Lys Val Ala
145                 150                 155                 160

Ser His Ala Pro Ser Leu Leu Arg Asp Val Phe His Thr Thr Val Asn
                165                 170                 175

Phe Ile Asn Gln Asn Leu Phe Ser Tyr Val Arg Asn Leu Val Arg Asn
                180                 185                 190

Glu Met Asp
        195

<210> SEQ ID NO 3
<211> LENGTH: 135
<212> TYPE: PRT
<213> ORGANISM: Homo sapiens

<400> SEQUENCE: 3

Gly Asn Arg Ser Ser His Ser Arg Leu Gly Arg Ile Glu Ala Asp Ser
  1               5                  10                  15

Glu Ser Gln Glu Asp Ile Ile Arg Asn Ile Ala Arg His Leu Ala Gln
                 20                  25                  30

Val Gly Asp Ser Met Asp Arg Ser Ile Pro Pro Gly Leu Val Asn Gly
             35                  40                  45

Leu Ala Leu Gln Leu Arg Asn Thr Ser Arg Ser Glu Glu Asp Arg Asn
```

-continued

```
                50                  55                  60
Arg Asp Leu Ala Thr Ala Leu Glu Gln Leu Leu Gln Ala Tyr Pro Arg
 65                  70                  75                  80

Asp Met Glu Lys Glu Lys Thr Met Leu Val Leu Ala Leu Leu Leu Ala
                 85                  90                  95

Lys Lys Val Ala Ser His Thr Pro Ser Leu Leu Arg Asp Val Phe His
                100                 105                 110

Thr Thr Val Asn Phe Ile Asn Gln Asn Leu Arg Thr Tyr Val Arg Ser
                115                 120                 125

Leu Ala Arg Asn Gly Met Asp
                130                 135

<210> SEQ ID NO 4
<211> LENGTH: 140
<212> TYPE: PRT
<213> ORGANISM: Homo sapiens

<400> SEQUENCE: 4

Gly Asn Arg Ser Ser His Ser Arg Leu Gly Arg Ile Glu Ala Asp Ser
  1                   5                  10                  15

Glu Ser Gln Glu Asp Ile Ile Arg Asn Ile Ala Arg His Leu Ala Gln
                 20                  25                  30

Val Gly Asp Ser Met Asp Arg Ser Ile Pro Pro Gly Leu Val Asn Gly
                 35                  40                  45

Leu Ala Leu Gln Leu Arg Asn Thr Ser Arg Ser Glu Glu Asp Arg Asn
                 50                  55                  60

Arg Asp Leu Ala Thr Ala Leu Glu Gln Leu Leu Gln Ala Tyr Pro Arg
 65                  70                  75                  80

Asp Met Glu Lys Glu Lys Thr Met Leu Val Leu Ala Leu Leu Leu Ala
                 85                  90                  95

Lys Lys Val Ala Ser His Thr Pro Ser Leu Leu Arg Asp Val Phe His
                100                 105                 110

Thr Thr Val Asn Phe Ile Asn Gln Asn Leu Arg Thr Tyr Val Arg Ser
                115                 120                 125

Leu Ala Arg Asn Val Arg Thr Leu Glu Gly Met Asp
                130                 135                 140

<210> SEQ ID NO 5
<211> LENGTH: 136
<212> TYPE: PRT
<213> ORGANISM: Mus musculus

<400> SEQUENCE: 5

Gly Ser Gln Ala Ser Arg Ser Phe Asn Gln Gly Arg Ile Glu Pro Asp
  1                   5                  10                  15

Ser Glu Ser Gln Glu Glu Ile Ile His Asn Ile Ala Arg His Leu Ala
                 20                  25                  30

Gln Ile Gly Asp Glu Met Asp His Asn Ile Gln Pro Thr Leu Val Arg
                 35                  40                  45

Gln Leu Ala Ala Gln Phe Met Asn Gly Ser Leu Ser Glu Glu Asp Lys
                 50                  55                  60

Arg Asn Cys Leu Ala Lys Ala Leu Asp Glu Val Lys Thr Ala Phe Pro
 65                  70                  75                  80

Arg Asp Met Glu Asn Asp Lys Ala Met Leu Ile Met Thr Met Leu Leu
                 85                  90                  95

Ala Lys Lys Val Ala Ser His Ala Pro Ser Leu Leu Arg Asp Val Phe
```

```
                    100                 105                 110
His Thr Thr Val Asn Phe Ile Asn Gln Asn Leu Phe Ser Tyr Val Arg
            115                 120                 125

Asn Leu Val Arg Asn Glu Met Asp
        130                 135

<210> SEQ ID NO 6
<211> LENGTH: 4
<212> TYPE: PRT
<213> ORGANISM: Artificial Sequence
<220> FEATURE:
<221> NAME/KEY: PEPTIDE
<222> LOCATION: (1)..(4)
<223> OTHER INFORMATION: Residue 3 is any amino acid
<220> FEATURE:
<223> OTHER INFORMATION: Description of Artificial Sequence: Caspase
      specificity sequence

<400> SEQUENCE: 6

Asp Glu Xaa Asp
  1

<210> SEQ ID NO 7
<211> LENGTH: 4
<212> TYPE: PRT
<213> ORGANISM: Homo sapiens

<400> SEQUENCE: 7

Leu Gln Thr Asp
```